(12) United States Patent
Shelton, IV et al.

(10) Patent No.: US 11,013,569 B2
(45) Date of Patent: May 25, 2021

(54) SURGICAL SYSTEMS WITH INTERCHANGEABLE MOTOR PACKS

(71) Applicant: Ethicon LLC, Guaynabo, PR (US)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/454,710

(22) Filed: Jun. 27, 2019

(65) Prior Publication Data
US 2020/0405425 A1 Dec. 31, 2020

(51) Int. Cl.
| | |
|---|---|
| *H02P 1/00* | (2006.01) |
| *A61B 34/00* | (2016.01) |
| *A61B 34/20* | (2016.01) |
| *A61B 34/35* | (2016.01) |
| *A61B 90/00* | (2016.01) |
| *A61B 17/00* | (2006.01) |
| *A61B 34/30* | (2016.01) |
| *A61B 90/30* | (2016.01) |

(52) U.S. Cl.
CPC .............. *A61B 34/74* (2016.02); *A61B 34/20* (2016.02); *A61B 34/25* (2016.02); *A61B 34/35* (2016.02); *A61B 90/361* (2016.02); *A61B 90/30* (2016.02); *A61B 90/37* (2016.02); *A61B 2017/00017* (2013.01); *A61B 2017/00398* (2013.01); *A61B 2017/00477* (2013.01); *A61B 2034/2048* (2016.02); *A61B 2034/2055* (2016.02); *A61B 2034/305* (2016.02); *A61B 2090/371* (2016.02)

(58) Field of Classification Search
CPC .................... A61B 34/30; A61B 34/35; A61B 2017/00734; A61B 34/75; A61B 34/20; A61B 34/25; A61B 43/35; A61B 2034/2048; A61B 2034/2055; A61B 2034/305; A61B 90/30; A61B 2017/00477; A61B 2017/00017; A61B 2017/00318; A61B 90/361; A61B 90/37; A61B 2090/371; G05B 15/02

See application file for complete search history.

(56) References Cited

U.S. PATENT DOCUMENTS

| | | |
|---|---|---|
| 7,982,776 B2 | 7/2011 | Dunki-Jacobs et al. |
| 7,995,045 B2 | 8/2011 | Dunki-Jacobs |
| 8,912,746 B2 | 12/2014 | Reid et al. |

(Continued)

OTHER PUBLICATIONS

IEEE Std 802.3-2012 (Revision of IEEE Std 802.3-2008, published Dec. 28, 2012.

(Continued)

*Primary Examiner* — Karen Masih

(57) ABSTRACT

A detachable motor pack, for use with multiple electrical surgical instruments, includes a housing; a plurality of motors retained within the housing; a controller configured to control one or more operations of the plurality of motors; a first interface portion, wherein the first interface portion is configured to releasably attach to a hand-held surgical instrument and to a robotic surgical instrument; and a second interface portion, wherein the second interface portion is configured to releasably attach to a first surgical tool of the hand-held surgical instrument and to a second surgical tool of the robotic surgical instrument.

18 Claims, 27 Drawing Sheets

(56) References Cited

U.S. PATENT DOCUMENTS

| | | |
|---|---|---|
| 9,060,775 B2 | 6/2015 | Wiener et al. |
| 9,072,535 B2 | 7/2015 | Shelton, IV et al. |
| 9,072,536 B2 | 7/2015 | Shelton, IV et al. |
| 9,204,879 B2 | 12/2015 | Shelton, IV |
| 9,345,481 B2 | 5/2016 | Hall et al. |
| 9,561,038 B2 | 2/2017 | Shelton, IV et al. |
| 9,572,552 B1 * | 2/2017 | Bodor ............... H01M 10/6572 |
| 9,757,128 B2 | 9/2017 | Baber et al. |
| 9,937,626 B2 | 4/2018 | Rockrohr |
| 10,098,527 B2 | 10/2018 | Weisenburgh, II et al. |
| 10,376,338 B2 | 8/2019 | Taylor et al. |
| 10,390,895 B2 | 8/2019 | Henderson et al. |
| 10,420,620 B2 | 9/2019 | Rockrohr |
| 10,507,068 B2 | 12/2019 | Kopp et al. |
| 10,517,686 B2 | 12/2019 | Vokrot et al. |
| 10,548,504 B2 | 2/2020 | Shelton, IV et al. |
| 10,624,691 B2 | 4/2020 | Wiener et al. |
| 10,639,111 B2 | 5/2020 | Kopp |
| 10,653,489 B2 | 5/2020 | Kopp |
| 10,667,877 B2 | 6/2020 | Kapadia |
| 10,716,639 B2 | 7/2020 | Kapadia et al. |
| 10,743,872 B2 | 8/2020 | Leimbach et al. |
| 10,779,849 B2 | 9/2020 | Shelton, IV et al. |
| 10,779,897 B2 | 9/2020 | Rockrohr |
| 10,779,900 B2 | 9/2020 | Pedros et al. |
| 10,806,454 B2 | 10/2020 | Kopp |
| 10,849,700 B2 | 12/2020 | Kopp et al. |
| 2011/0306840 A1 | 12/2011 | Allen et al. |
| 2014/0263552 A1 | 9/2014 | Hall et al. |
| 2016/0175062 A1 * | 6/2016 | Limon ............... B08B 3/04 134/32 |
| 2017/0202591 A1 | 7/2017 | Shelton, IV et al. |
| 2017/0296213 A1 | 10/2017 | Swensgard et al. |
| 2018/0263717 A1 | 9/2018 | Kopp |
| 2018/0360452 A1 | 12/2018 | Shelton, IV et al. |
| 2019/0000446 A1 | 1/2019 | Shelton, IV et al. |
| 2019/0000478 A1 | 1/2019 | Messerly et al. |
| 2019/0053866 A1 | 2/2019 | Seow et al. |
| 2019/0104919 A1 | 4/2019 | Shelton, IV et al. |
| 2019/0200844 A1 | 7/2019 | Shelton, IV et al. |
| 2019/0200981 A1 | 7/2019 | Harris et al. |
| 2019/0200998 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201136 A1 | 7/2019 | Shelton, IV et al. |
| 2019/0201137 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0208641 A1 | 7/2019 | Yates et al. |
| 2020/0405421 A1 * | 12/2020 | Luck ............... A61B 34/70 |

OTHER PUBLICATIONS

"ATM-MPLS Network Interworking Version 2.0, af-aic-0178.001" ATM Standard, The ATM Forum Technical Committee, published Aug. 2003.

* cited by examiner

SURGICAL SYSTEMS WITH INTERCHANGEABLE MOTOR PACKS

BACKGROUND

The present disclosure relates to robotic surgical systems. Robotic surgical systems can include a central control unit, a surgeon's command console, and a robot having one or more robotic arms. Robotic surgical tools can be releasably mounted to the robotic arm(s). The number and type of robotic surgical tools can depend on the type of surgical procedure. Robotic surgical systems can be used in connection with one or more displays and/or one or more handheld surgical instruments during a surgical procedure.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

DESCRIPTION

Figure 1:
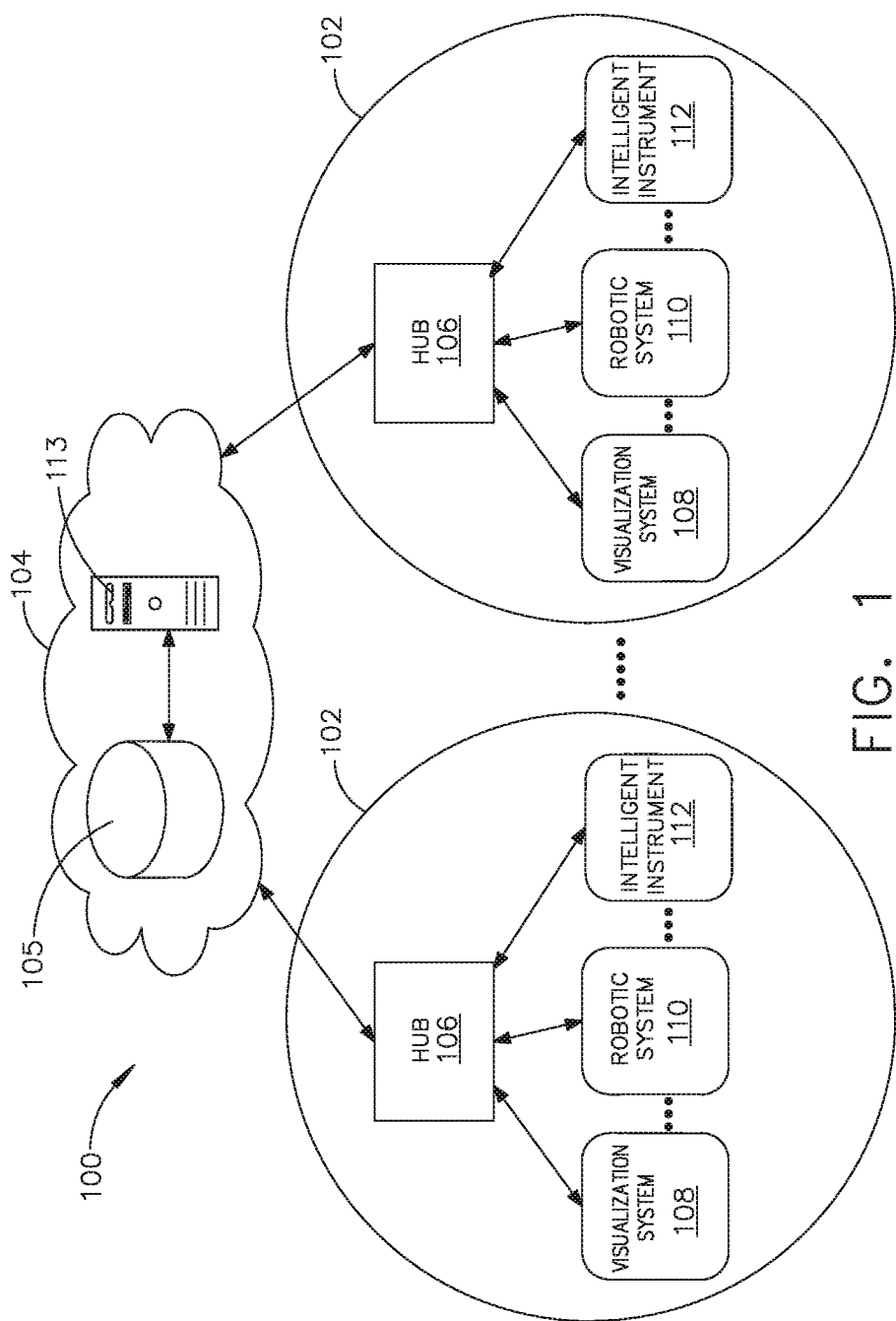
FIG. 1 is a block diagram of a computer-implemented interactive surgical system, in accordance with at least one aspect of the present disclosure.

Applicant of the present application owns the following U.S. Patent Applications, filed on Jun. 27, 2019, the disclosure of each of which is herein incorporated by reference in its entirety:

U.S. patent application Ser. No. 16/454,702, titled METHOD OF USING A SURGICAL MODULAR ROBOTIC ASSEMBLY;

U.S. patent application Ser. No. 16/454,715, titled COOPERATIVE ROBOTIC SURGICAL SYSTEMS;

U.S. patent application Ser. No. 16/454,740, titled HEAT EXCHANGE SYSTEMS FOR ROBOTIC SURGICAL SYSTEMS;

U.S. patent application Ser. No. 16/454,757, titled DETERMINING ROBOTIC SURGICAL ASSEMBLY COUPLING STATUS;

U.S. patent application Ser. No. 16/454,780, titled ROBOTIC SURGICAL ASSEMBLY COUPLING SAFETY MECHANISMS;

U.S. patent application Ser. No. 16/454,707, titled ROBOTIC SURGICAL SYSTEM WITH SAFETY AND COOPERATIVE SENSING CONTROL;

U.S. patent application Ser. No. 16/454,726, titled ROBOTIC SURGICAL SYSTEM FOR CONTROLLING CLOSE OPERATION OF END-EFFECTORS;

U.S. patent application Ser. No. 16/454,737, titled ROBOTIC SURGICAL SYSTEM WITH LOCAL SENSING OF FUNCTIONAL PARAMETERS BASED ON MEASUREMENTS OF MULTIPLE PHYSICAL INPUTS;

U.S. patent application Ser. No. 16/454,751, titled COOPERATIVE OPERATION OF ROBOTIC ARMS;

U.S. patent application Ser. No. 16/454,760, titled SURGICAL INSTRUMENT DRIVE SYSTEMS;

U.S. patent application Ser. No. 16/454,769, titled SURGICAL INSTRUMENT DRIVE SYSTEMS WITH CABLE-TIGHTENING SYSTEM;

U.S. patent application Ser. No. 16/454,727, titled VISUALIZATION SYSTEM WITH AUTOMATIC CONTAMINATION DETECTION AND CLEANING CONTROLS; and U.S. patent application Ser. No. 16/454,741, titled MULTI-ACCESS PORT FOR SURGICAL ROBOTIC SYSTEMS.

Applicant of the present application owns the following U.S. Patent Applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY;

U.S. patent application Ser. No. 16/209,395, titled METHOD OF HUB COMMUNICATION;

U.S. patent application Ser. No. 16/209,403, titled METHOD OF CLOUD BASED DATA ANALYTICS FOR USE WITH THE HUB;

U.S. patent application Ser. No. 16/209,407, titled METHOD OF ROBOTIC HUB COMMUNICATION, DETECTION, AND CONTROL;

U.S. patent application Ser. No. 16/209,416, titled METHOD OF HUB COMMUNICATION, PROCESSING, DISPLAY, AND CLOUD ANALYTICS;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, titled METHOD FOR SMOKE EVACUATION FOR SURGICAL HUB;

U.S. patent application Ser. No. 16/209,453, titled METHOD FOR CONTROLLING SMART ENERGY DEVICES;

U.S. patent application Ser. No. 16/209,458, titled METHOD FOR SMART ENERGY DEVICE INFRASTRUCTURE;

U.S. patent application Ser. No. 16/209,465, titled METHOD FOR ADAPTIVE CONTROL SCHEMES FOR SURGICAL NETWORK CONTROL AND INTERACTION;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, titled METHOD FOR FACILITY DATA COLLECTION AND INTERPRETATION; and U.S. patent application Ser. No. 16/209,491, titled METHOD FOR CIRCULAR STAPLER CONTROL ALGORITHM ADJUSTMENT BASED ON SITUATIONAL AWARENESS.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
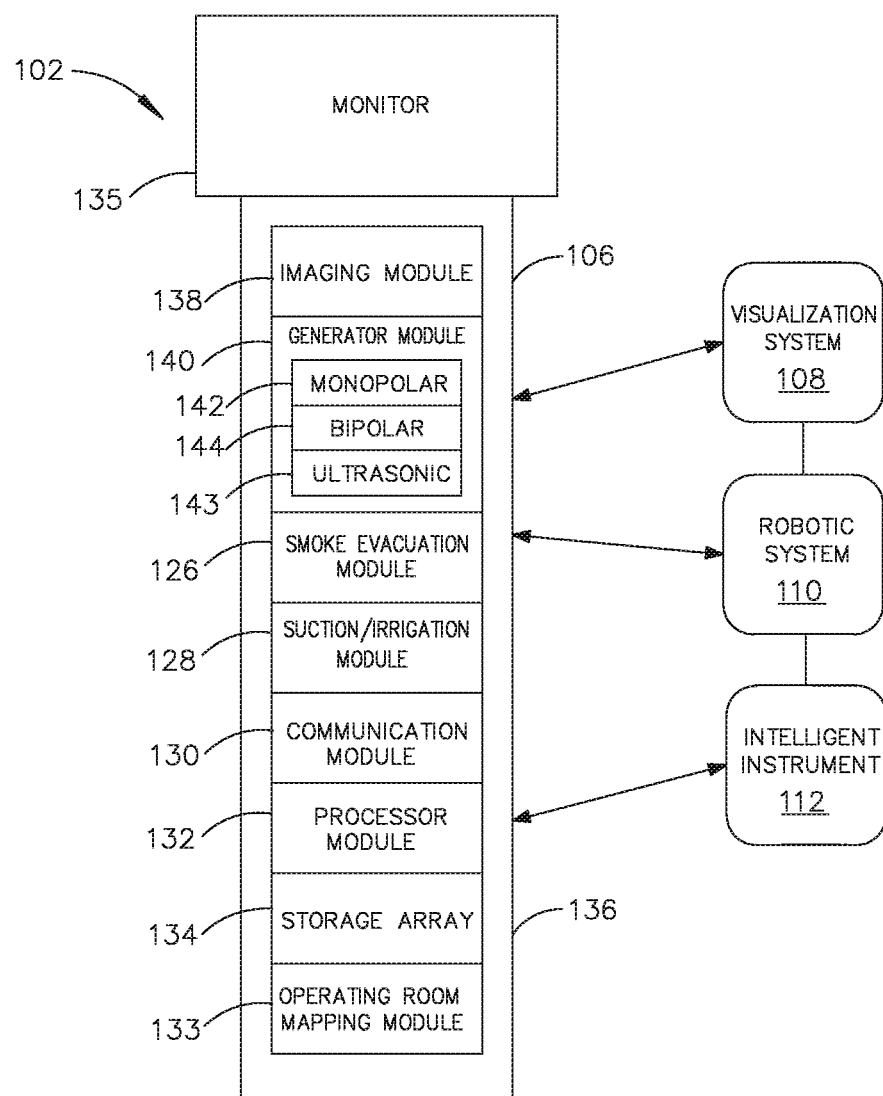
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
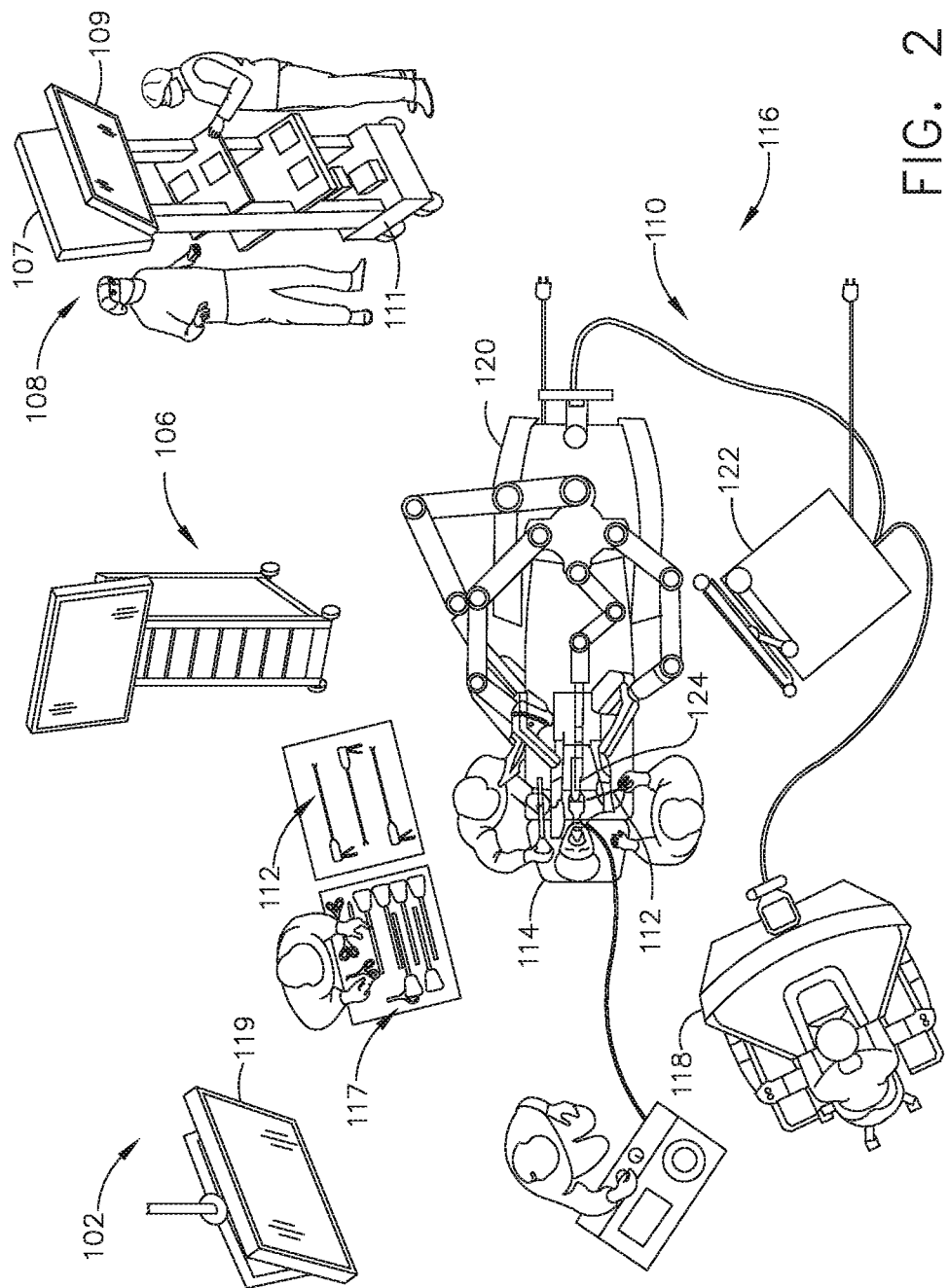
FIG. 2 is a surgical system being used to perform a surgical procedure in an operating room, in accordance with at least one aspect of the present disclosure.

In various aspects, the visualization system 108 includes one or more imaging sensors, one or more image processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snap-shot of a surgical site, as recorded by an imaging device 124, on a non-sterile display 107 or 109, while maintaining a live feed of the surgical site on the primary display 119. The snap-shot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snap-shot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. In various aspects, the hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane with external and wireless communication headers to enable the removable attachment of the modules 140, 126, 128 and interactive communication therebetween.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Robotic Surgical System

Figure 4:
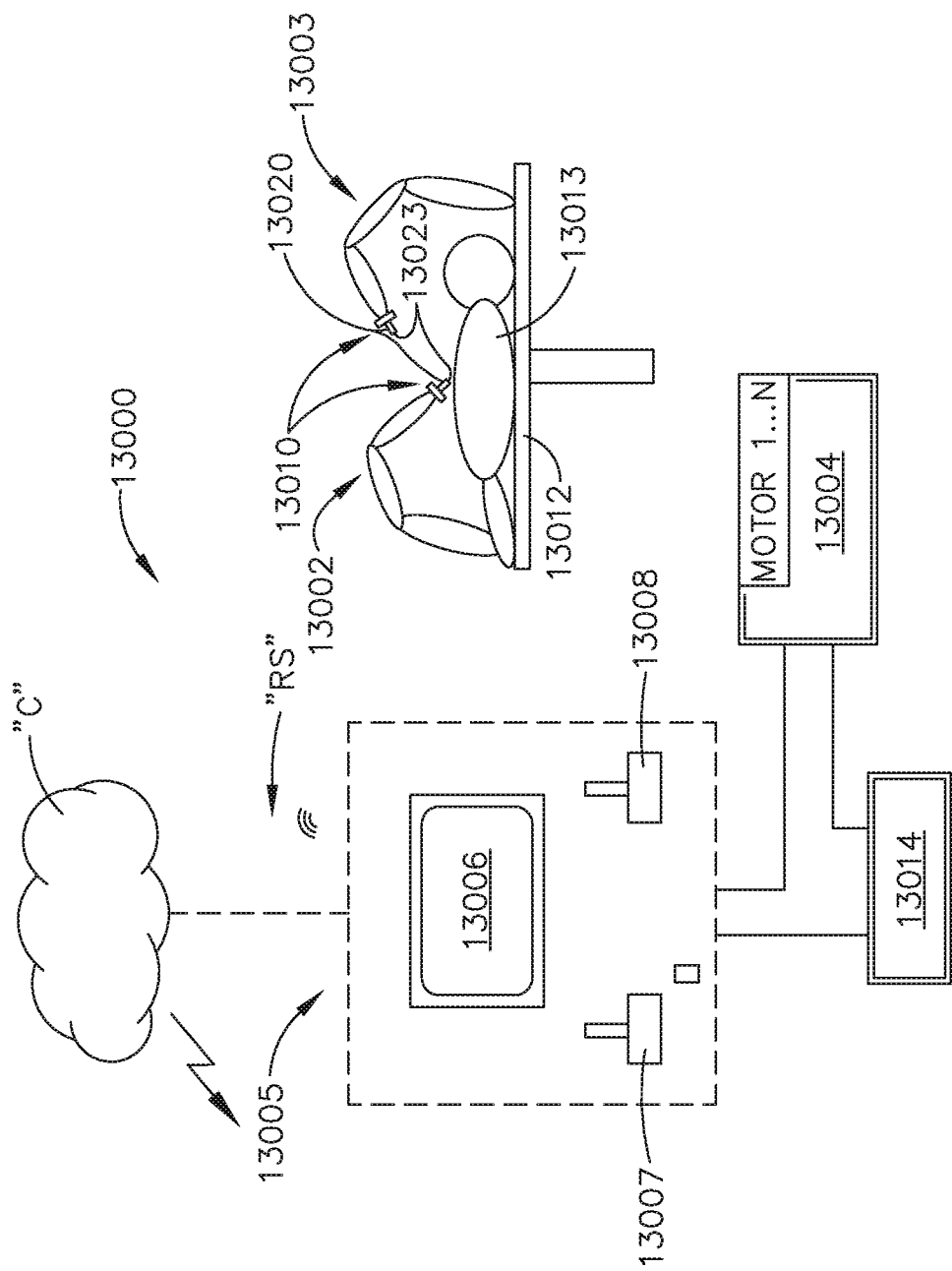
FIG. 4 is a schematic of a robotic surgical system, in accordance with at least one aspect of the present disclosure.
Figure 5:
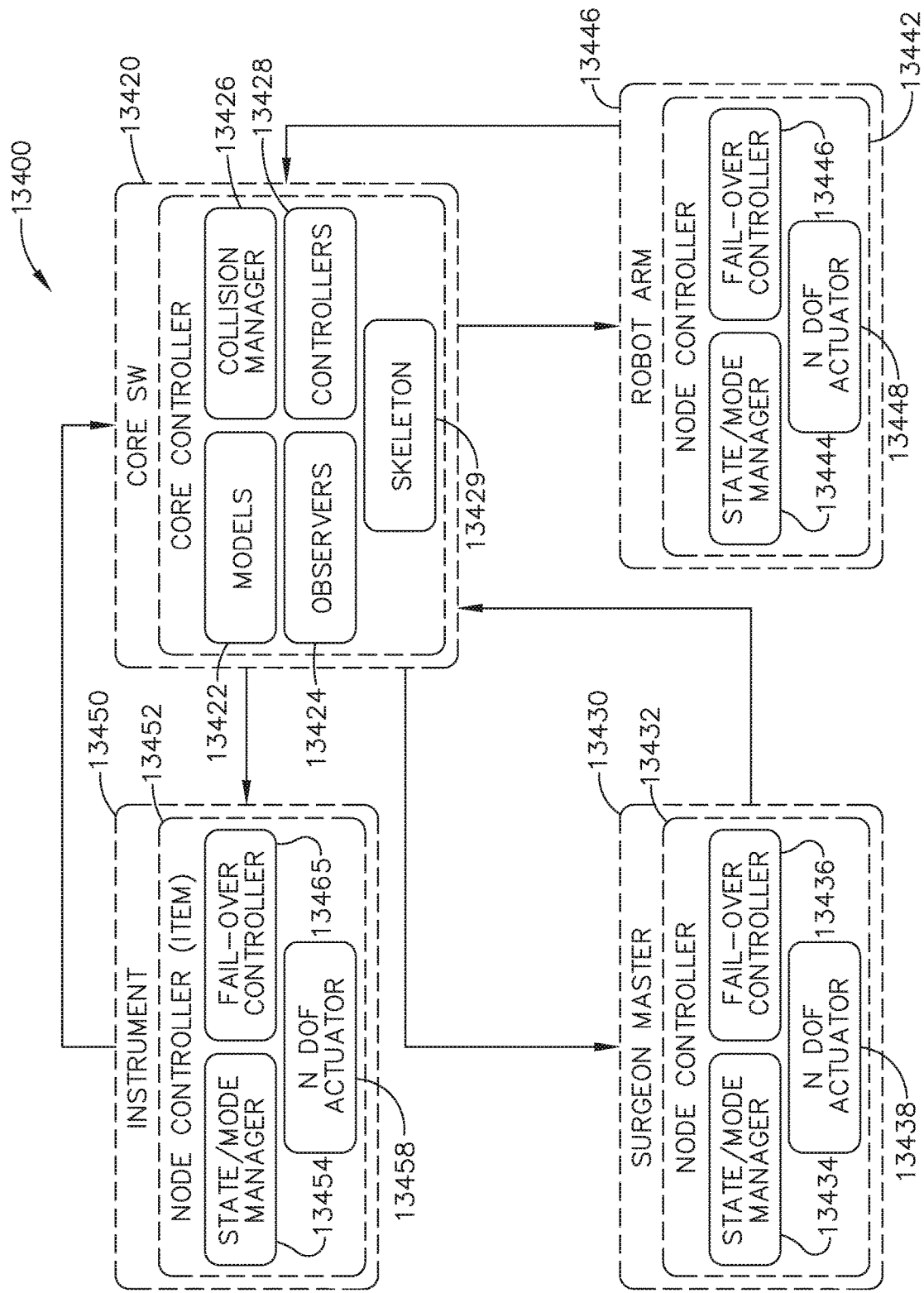
FIG. 5 is a block diagram of control components for the robotic surgical system of FIG. 4, in accordance with at least one aspect of the present disclosure.

An example robotic surgical system is depicted in FIGS. 4 and 5. With reference to FIG. 4, the robotic surgical system 13000 includes robotic arms 13002, 13003, a control device 13004, and a console 13005 coupled to the control device 13004. As illustrated in FIG. 4, the surgical system 13000 is configured for use on a patient 13013 lying on a patient table 13012 for performance of a minimally invasive surgical operation. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003. Controls for a surgeon's console, such as the console 13005, are further described in International Patent Publication No. WO2017/075121, filed Oct. 27, 2016, titled HAPTIC FEEDBACK FOR A ROBOTIC SURGICAL SYSTEM INTERFACE, which is herein incorporated by reference in its entirety.

Each of the robotic arms 13002, 13003 is made up of a plurality of members connected through joints and includes a surgical assembly 13010 connected to a distal end of a corresponding robotic arm 13002, 13003. Support of multiple arms is further described in U.S. Patent Application Publication No. 2017/0071693, filed Nov. 11, 2016, titled SURGICAL ROBOTIC ARM SUPPORT SYSTEMS AND METHODS OF USE, which is herein incorporated by reference in its entirety. Various robotic arm configurations are further described in International Patent Publication No. WO2017/044406, filed Sep. 6, 2016, titled ROBOTIC SURGICAL CONTROL SCHEME FOR MANIPULATING ROBOTIC END EFFECTORS, which is herein incorporated by reference in its entirety. In an exemplification, the surgical assembly 13010 includes a surgical instrument 13020 supporting an end effector 13023. Although two robotic arms 13002, 13003, are depicted, the surgical system 13000 may include a single robotic arm or more than two robotic arms 13002, 13003. Additional robotic arms are likewise connected to the control device 13004 and are telemanipulatable via the console 13005. Accordingly, one or more additional surgical assemblies 13010 and/or surgical instruments 13020 may also be attached to the additional robotic arm(s).

The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008. The control device 13004 may also be configured to regulate movement of the robotic arms 13002, 13003 and/or of the drives.

The control device 13004 may control a plurality of motors (for example, Motor I . . . n) with each motor configured to drive a pushing or a pulling of one or more cables, such as cables coupled to the end effector 13023 of the surgical instrument 13020. In use, as these cables are pushed and/or pulled, the one or more cables affect operation and/or movement of the end effector 13023. The control device 13004 coordinates the activation of the various motors to coordinate a pushing or a pulling motion of one or more cables in order to coordinate an operation and/or movement of one or more end effectors 13023. For example, articulation of an end effector by a robotic assembly such as the surgical assembly 13010 is further described in U.S. Patent Application Publication No. 2016/0303743, filed Jun. 6, 2016, titled WRIST AND JAW ASSEMBLIES FOR ROBOTIC SURGICAL SYSTEMS and in International Patent Publication No. WO2016/144937, filed Mar. 8, 2016, titled MEASURING HEALTH OF A CONNECTOR MEMBER OF A ROBOTIC SURGICAL SYSTEM, each of which is herein incorporated by reference in its entirety. In an exemplification, each motor is configured to actuate a drive rod or a lever arm to affect operation and/or movement of end effectors 13023 in addition to, or instead of, one or more cables.

Driver configurations for surgical instruments, such as drive arrangements for a surgical end effector, are further described in International Patent Publication No. WO2016/

183054, filed May 10, 2016, titled COUPLING INSTRUMENT DRIVE UNIT AND ROBOTIC SURGICAL INSTRUMENT, International Patent Publication No. WO2016/205266, filed Jun. 15, 2016, titled ROBOTIC SURGICAL SYSTEM TORQUE TRANSDUCTION SENSING, International Patent Publication No. WO2016/205452, filed Jun. 16, 2016, titled CONTROLLING ROBOTIC SURGICAL INSTRUMENTS WITH BIDIRECTIONAL COUPLING, and International Patent Publication No. WO2017/053507, filed Sep. 22, 2016, titled ELASTIC SURGICAL INTERFACE FOR ROBOTIC SURGICAL SYSTEMS, each of which is herein incorporated by reference in its entirety. The modular attachment of surgical instruments to a driver is further described in International Patent Publication No. WO2016/209769, filed Jun. 20, 2016, titled ROBOTIC SURGICAL ASSEMBLIES, which is herein incorporated by reference in its entirety. Housing configurations for a surgical instrument driver and interface are further described in International Patent Publication No. WO2016/144998, filed Mar. 9, 2016, titled ROBOTIC SURGICAL SYSTEMS, INSTRUMENT DRIVE UNITS, AND DRIVE ASSEMBLIES, which is herein incorporated by reference in its entirety. Various surgical instrument configurations for use with the robotic arms 13002, 13003 are further described in International Patent Publication No. WO2017/053358, filed Sep. 21, 2016, titled SURGICAL ROBOTIC ASSEMBLIES AND INSTRUMENT ADAPTERS THEREOF and International Patent Publication No. WO2017/053363, filed Sep. 21, 2016, titled ROBOTIC SURGICAL ASSEMBLIES AND INSTRUMENT DRIVE CONNECTORS THEREOF, each of which is herein incorporated by reference in its entirety. Bipolar instrument configurations for use with the robotic arms 13002, 13003 are further described in International Patent Publication No. WO2017/053698, filed Sep. 23, 2016, titled ROBOTIC SURGICAL ASSEMBLIES AND ELECTROMECHANICAL INSTRUMENTS THEREOF, which is herein incorporated by reference in its entirety. Shaft arrangements for use with the robotic arms 13002, 13003 are further described in International Patent Publication No. WO2017/116793, filed Dec. 19, 2016, titled ROBOTIC SURGICAL SYSTEMS AND INSTRUMENT DRIVE ASSEMBLIES, which is herein incorporated by reference in its entirety.

The control device 13004 includes any suitable logic control circuit adapted to perform calculations and/or operate according to a set of instructions. The control device 13004 can be configured to communicate with a remote system "RS," either via a wireless (e.g., Wi-Fi, Bluetooth, LTE, etc.) and/or wired connection. The remote system "RS" can include data, instructions and/or information related to the various components, algorithms, and/or operations of system 13000. The remote system "RS" can include any suitable electronic service, database, platform, cloud "C" (see FIG. 4), or the like. The control device 13004 may include a central processing unit operably connected to memory. The memory may include transitory type memory (e.g., RAM) and/or non-transitory type memory (e.g., flash media, disk media, etc.). In some exemplifications, the memory is part of, and/or operably coupled to, the remote system "RS."

The control device 13004 can include a plurality of inputs and outputs for interfacing with the components of the system 13000, such as through a driver circuit. The control device 13004 can be configured to receive input signals and/or generate output signals to control one or more of the various components (e.g., one or more motors) of the system 13000. The output signals can include, and/or can be based upon, algorithmic instructions which may be pre-programmed and/or input by a user. The control device 13004 can be configured to accept a plurality of user inputs from a user interface (e.g., switches, buttons, touch screen, etc. of operating the console 13005) which may be coupled to remote system "RS."

A memory 13014 can be directly and/or indirectly coupled to the control device 13004 to store instructions and/or databases including pre-operative data from living being(s) and/or anatomical atlas(es). The memory 13014 can be part of, and/or or operatively coupled to, remote system "RS."

In accordance with an exemplification, the distal end of each robotic arm 13002, 13003 is configured to releasably secure the end effector 13023 (or other surgical tool) therein and may be configured to receive any number of surgical tools or instruments, such as a trocar or retractor, for example.

A simplified functional block diagram of a system architecture 13400 of the robotic surgical system 13010 is depicted in FIG. 5. The system architecture 13400 includes a core module 13420, a surgeon master module 13430, a robotic arm module 13440, and an instrument module 13450. The core module 13420 serves as a central controller for the robotic surgical system 13000 and coordinates operations of all of the other modules 13430, 13440, 13450. For example, the core module 13420 maps control devices to the arms 13002, 13003, determines current status, performs all kinematics and frame transformations, and relays resulting movement commands. In this regard, the core module 13420 receives and analyzes data from each of the other modules 13430, 13440, 13450 in order to provide instructions or commands to the other modules 13430, 13440, 13450 for execution within the robotic surgical system 13000. Although depicted as separate modules, one or more of the modules 13420, 13430, 13440, and 13450 are a single component in other exemplifications.

The core module 13420 includes models 13422, observers 13424, a collision manager 13426, controllers 13428, and a skeleton 13429. The models 13422 include units that provide abstracted representations (base classes) for controlled components, such as the motors (for example, Motor I . . . n) and/or the arms 13002, 13003. The observers 13424 create state estimates based on input and output signals received from the other modules 13430, 13440, 13450. The collision manager 13426 prevents collisions between components that have been registered within the system 13010. The skeleton 13429 tracks the system 13010 from a kinematic and dynamics point of view. For example, the kinematics item may be implemented either as forward or inverse kinematics, in an exemplification. The dynamics item may be implemented as algorithms used to model dynamics of the system's components.

The surgeon master module 13430 communicates with surgeon control devices at the console 13005 and relays inputs received from the console 13005 to the core module 13420. In accordance with an exemplification, the surgeon master module 13430 communicates button status and control device positions to the core module 13420 and includes a node controller 13432 that includes a state/mode manager 13434, a fail-over controller 13436, and a N-degree of freedom ("DOF") actuator 13438.

The robotic arm module 13440 coordinates operation of a robotic arm subsystem, an arm cart subsystem, a set up arm, and an instrument subsystem in order to control movement of a corresponding arm 13002, 13003. Although a single robotic arm module 13440 is included, it will be appreciated that the robotic arm module 13440 corresponds to and controls a single arm. As such, additional robotic arm modules 13440 are included in configurations in which the system 13010 includes multiple arms 13002, 13003. The robotic arm module 13440 includes a node controller 13442, a state/mode manager 13444, a fail-over controller 13446, and a N-degree of freedom ("DOF") actuator 13348.

The instrument module 13450 controls movement of an instrument and/or tool component attached to the arm 13002, 13003. The instrument module 13450 is configured to correspond to and control a single instrument. Thus, in configurations in which multiple instruments are included, additional instrument modules 13450 are likewise included. In an exemplification, the instrument module 13450 obtains and communicates data related to the position of the end effector or jaw assembly (which may include the pitch and yaw angle of the jaws), the width of or the angle between the jaws, and the position of an access port. The instrument module 13450 has a node controller 13452, a state/mode manager 13454, a fail-over controller 13456, and a N-degree of freedom ("DOF") actuator 13458.

The position data collected by the instrument module 13450 is used by the core module 13420 to determine when the instrument is within the surgical site, within a cannula, adjacent to an access port, or above an access port in free space. The core module 13420 can determine whether to provide instructions to open or close the jaws of the instrument based on the positioning thereof. For example, when the position of the instrument indicates that the instrument is within a cannula, instructions are provided to maintain a jaw assembly in a closed position. When the position of the instrument indicates that the instrument is outside of an access port, instructions are provided to open the jaw assembly.

Additional features and operations of a robotic surgical system, such as the surgical robot system depicted in FIGS. 4 and 5, are further described in the following references, each of which is herein incorporated by reference in its entirety:

U.S. Pat. No. 7,995,045, which issued Aug. 9, 2011, titled WRIST AND JAW ASSEMBLIES FOR ROBOTIC SURGICAL SYSTEMS;

U.S. Patent Application Publication No. 2017/0071693, filed Nov. 11, 2016, titled SURGICAL ROBOTIC ARM SUPPORT SYSTEMS AND METHODS OF USE;

International Patent Publication No. WO2016/144937, filed Mar. 8, 2016, titled MEASURING HEALTH OF A CONNECTOR MEMBER OF A ROBOTIC SURGICAL SYSTEM;

International Patent Publication No. WO2016/144998, filed Mar. 9, 2016, titled ROBOTIC SURGICAL SYSTEMS, INSTRUMENT DRIVE UNITS, AND DRIVE ASSEMBLIES;

International Patent Publication No. WO2016/183054, filed May 10, 2016, titled COUPLING INSTRUMENT DRIVE UNIT AND ROBOTIC SURGICAL INSTRUMENT;

International Patent Publication No. WO2016/205266, filed Jun. 15, 2016, titled ROBOTIC SURGICAL SYSTEM TORQUE TRANSDUCTION SENSING;

International Patent Publication No. WO2016/205452, filed Jun. 16, 2016, titled CONTROLLING ROBOTIC SURGICAL INSTRUMENTS WITH BIDIRECTIONAL COUPLING;

International Patent Publication No. WO2016/209769, filed Jun. 20, 2016, titled ROBOTIC SURGICAL ASSEMBLIES;

International Patent Publication No. WO2017/044406, filed Sep. 6, 2016, titled ROBOTIC SURGICAL CONTROL SCHEME FOR MANIPULATING ROBOTIC END EFFECTORS;

International Patent Publication No. WO2017/053358, filed Sep. 21, 2016, titled SURGICAL ROBOTIC ASSEMBLIES AND INSTRUMENT ADAPTERS THEREOF;

International Patent Publication No. WO2017/053363, filed Sep. 21, 2016, titled ROBOTIC SURGICAL ASSEMBLIES AND INSTRUMENT DRIVE CONNECTORS THEREOF;

International Patent Publication No. WO2017/053507, filed Sep. 22, 2016, titled ELASTIC SURGICAL INTERFACE FOR ROBOTIC SURGICAL SYSTEMS;

International Patent Publication No. WO2017/053698, filed Sep. 23, 2016, titled ROBOTIC SURGICAL ASSEMBLIES AND ELECTROMECHANICAL INSTRUMENTS THEREOF;

International Patent Publication No. WO2017/075121, filed Oct. 27, 2016, titled HAPTIC FEEDBACK CONTROLS FOR A ROBOTIC SURGICAL SYSTEM INTERFACE;

International Patent Publication No. WO2017/116793, filed Dec. 19, 2016, titled ROBOTIC SURGICAL SYSTEMS AND INSTRUMENT DRIVE ASSEMBLIES.

The robotic surgical systems and features disclosed herein can be employed with the robotic surgical system of FIGS. 4 and 5. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, and/or the robotic hub 222, for example.

In various instances, a robotic surgical system can include a robotic control tower, which can house the control unit of the system. For example, the control unit 13004 of the robotic surgical system 13000 (FIG. 4) can be housed within a robotic control tower. The robotic control tower can include a robotic hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, suction module, an irrigation module, a smoke evacuation module, and/or a communication module.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices to the robotic system based on the synthesized data. In various instances, a sensor system encompassing a plurality of sensors distributed throughout the robotic system can provide data, images, and/or other information to the situational awareness module. Such a situational awareness module can be incorporated into a control unit, such as the control unit 13004, for example. In various instances, the situational awareness module can obtain data and/or information from a non-robotic surgical hub and/or a cloud, such as the surgical hub 106 (FIG. 1), the surgical hub 206 (FIG. 10), the cloud 104 (FIG. 1), and/or the cloud 204 (FIG. 9), for example. Situational awareness of a surgical system is further disclosed herein and in U.S. Provisional Patent Application Ser. No. 62/611,341, titled INTERACTIVE SURGICAL PLATFORM, filed Dec. 28, 2017, and U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

In certain instances, the activation of a surgical tool at certain times during a surgical procedure and/or for certain durations may cause tissue trauma and/or may prolong a surgical procedure. For example, a robotic surgical system can utilize an electrosurgical tool having an energy delivery surface that should only be energized when a threshold condition is met. In one example, the energy delivery surface should only be activated when the energy delivery surface is in contact with the appropriate, or targeted, tissue. As another example, a robotic surgical system can utilize a suction element that should only be activated when a threshold condition is met, such as when an appropriate volume of fluid is present. Due to visibility restrictions, evolving situations, and the multitude of moving parts during a robotic surgical procedure, it can be difficult for a clinician to determine and/or monitor certain conditions at the surgical site. For example, it can be difficult to determine if an energy delivery surface of an electrosurgical tool is in contact with tissue. It can also be difficult to determine if a particular suctioning pressure is sufficient for the volume of fluid in the proximity of the suctioning port.

Moreover, a plurality of surgical devices can be used in certain robotic surgical procedures. For example, a robotic surgical system can use one or more surgical tools during the surgical procedure. Additionally, one or more handheld instruments can also be used during the surgical procedure. One or more of the surgical devices can include a sensor. For example, multiple sensors can be positioned around the surgical site and/or the operating room. A sensor system including the one or more sensors can be configured to detect one or more conditions at the surgical site. For example, data from the sensor system can determine if a surgical tool mounted to the surgical robot is being used and/or if a feature of the surgical tool should be activated. More specifically, a sensor system can detect if an electrosurgical device is positioned in abutting contact with tissue, for example. As another example, a sensor system can detect if a suctioning element of a surgical tool is applying a sufficient suctioning force to fluid at the surgical site.

When in an automatic activation mode, the robotic surgical system can automatically activate one or more features of one or more surgical tools based on data, images, and/or other information received from the sensor system. For example, an energy delivery surface of an electrosurgical tool can be activated upon detecting that the electrosurgical tool is in use (e.g. positioned in abutting contact with tissue). As another example, a suctioning element on a surgical tool can be activated when the suction port is moved into contact with a fluid. In certain instances, the surgical tool can be adjusted based on the sensed conditions.

A robotic surgical system incorporating an automatic activation mode can automatically provide a scenario-specific result based on detected condition(s) at the surgical site. The scenario-specific result can be outcome-based, for example, and can streamline the decision-making process of the clinician. In certain instances, such an automatic activation mode can improve the efficiency and/or effectiveness of the clinician. For example, the robotic surgical system can aggregate data to compile a more complete view of the surgical site and/or the surgical procedure in order to determine the best possible course of action. Additionally or alternatively, in instances in which the clinician makes fewer decisions, the clinician can be better focused on other tasks and/or can process other information more effectively.

Figure 6:
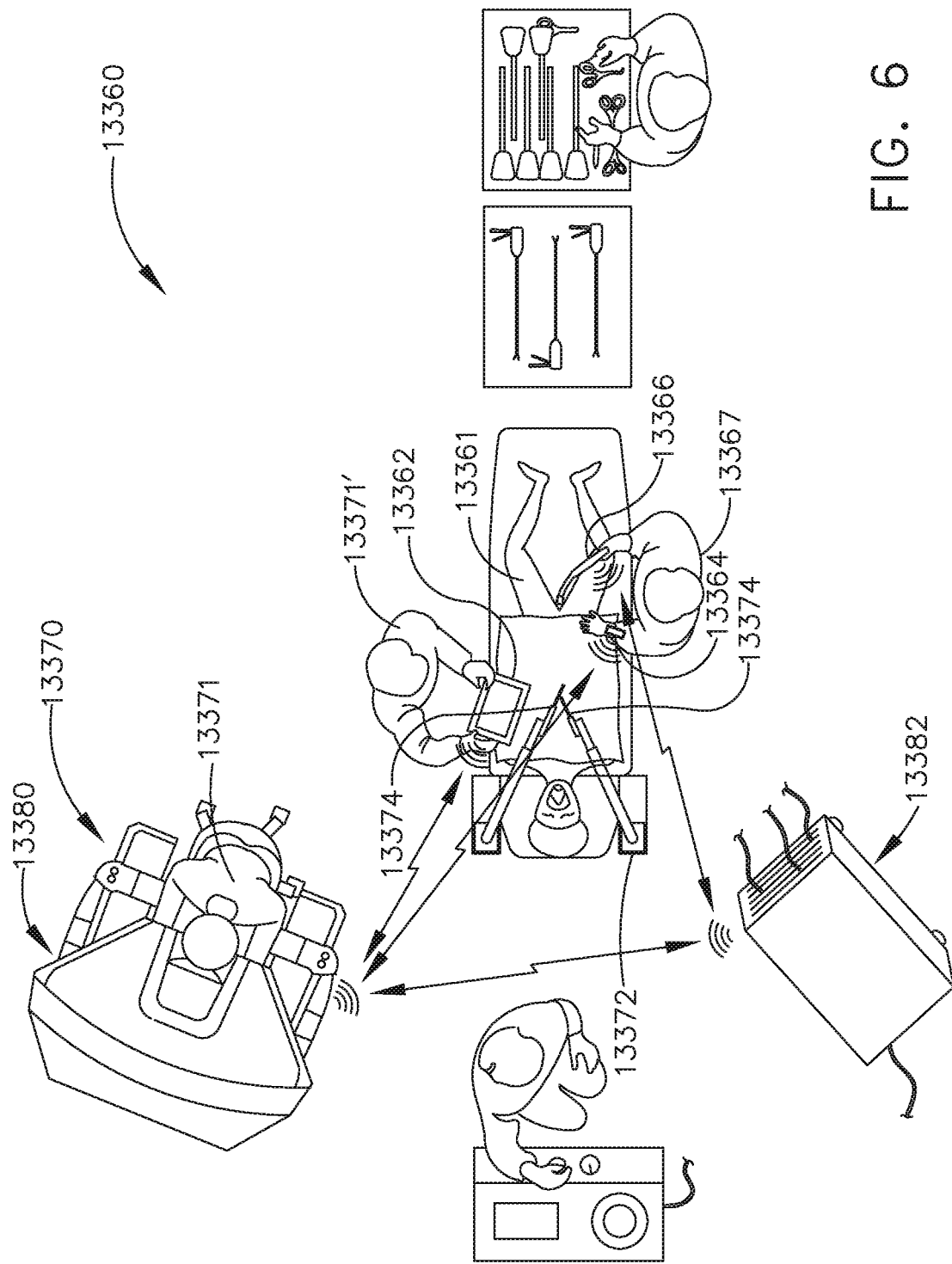
FIG. 6 is a schematic of a robotic surgical system during a surgical procedure including a plurality of hubs and interactive secondary displays, in accordance with at least one aspect of the present disclosure.
Figure 7:
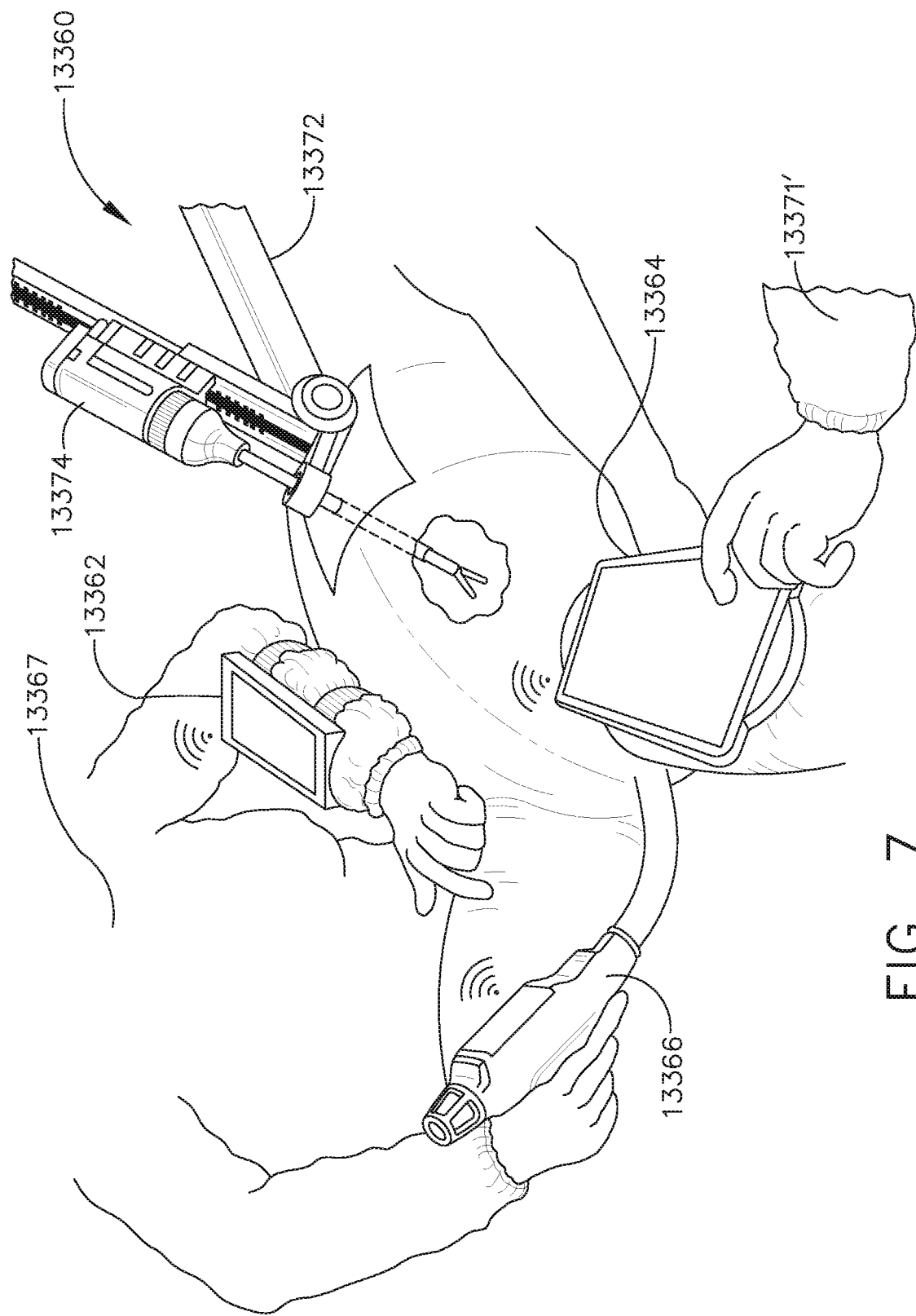
FIG. 7 is a detail view of the interactive secondary displays of FIG. 6, in accordance with at least one aspect of the present disclosure.

Referring primarily to FIGS. 6 and 7, hubs 13380, 13382 include wireless communication modules such that a wireless communication link is established between the two hubs 13380, 13382. Additionally, the robotic hub 13380 is in signal communication with the interactive secondary displays 13362, 13364 within the sterile field. The hub 13382 is in signal communication with the handheld surgical instrument 13366. If the surgeon 13371 moves over towards the patient 13361 and within the sterile field (as indicated by the reference character 13371'), the surgeon 13371 can use one of the wireless interactive displays 13362, 13364 to operate the robot 13372 away from the remote command console 13370. The plurality of secondary displays 13362, 13364 within the sterile field allows the surgeon 13371 to move away from the remote command console 13370 without losing sight of important information for the surgical procedure and controls for the robotic tools utilized therein.

The interactive secondary displays 13362, 13364 permit the clinician to step away from the remote command console 13370 and into the sterile field while maintaining control of the robot 13372. For example, the interactive secondary displays 13362, 13364 allow the clinician to maintain cooperative and/or coordinated control over the powered handheld surgical instrument(s) 13366 and the robotic surgical system at the same time. In various instances, information is communicated between the robotic surgical system, one or more powered handheld surgical instruments 13366, surgical hubs 13380, 13382, and the interactive secondary displays 13362, 13364. Such information may include, for example, the images on the display of the robotic surgical system and/or the powered handheld surgical instruments, a parameter of the robotic surgical system and/or the powered handheld surgical instruments, and/or a control command for the robotic surgical system and/or the powered handheld surgical instruments.

In various instances, the control unit of the robotic surgical system (e.g. the control unit 13113 of the robotic surgical system 13110) is configured to communicate at least one display element from the surgeon's command console (e.g. the console 13116) to an interactive secondary display (e.g. the displays 13362, 13364). In other words, a portion of the display at the surgeon's console is replicated on the display of the interactive secondary display, integrating the robot display with the interactive secondary display. The replication of the robot display on to the display of the interactive secondary display allows the clinician to step away from the remote command console without losing the visual image that is displayed there. For example, at least one of the interactive secondary displays 13362, 13364 can display information from the robot, such as information from the robot display and/or the surgeon's command console 13370.

In various instances, the interactive secondary displays 13362, 13364 are configured to control and/or adjust at least one operating parameter of the robotic surgical system. Such control can occur automatically and/or in response to a clinician input. Interacting with a touch-sensitive screen and/or buttons on the interactive secondary display(s) 13362, 13364, the clinician is able to input a command to control movement and/or functionality of the one or more robotic tools. For example, when utilizing a handheld surgical instrument 13366, the clinician may want to move the robotic tool 13374 to a different position. To control the robotic tool 13374, the clinician applies an input to the interactive secondary display(s) 13362, 13364, and the respective interactive secondary display(s) 13362, 13364 communicates the clinician input to the control unit of the robotic surgical system in the robotic hub 13380.

In various instances, a clinician positioned at the remote command console 13370 of the robotic surgical system can manually override any robot command initiated by a clinician input on the one or more interactive secondary displays 13362, 13364. For example, when a clinician input is received from the one or more interactive secondary displays 13362, 13364, a clinician positioned at the remote command console 13370 can either allow the command to be issued and the desired function performed or the clinician can override the command by interacting with the remote command console 13370 and prohibiting the command from being issued.

In certain instances, a clinician within the sterile field can be required to request permission to control the robot 13372 and/or the robotic tool 13374 mounted thereto. The surgeon 13371 at the remote command console 13370 can grant or deny the clinician's request. For example, the surgeon can receive a pop-up or other notification indicating the permission is being requested by another clinician operating a handheld surgical instrument and/or interacting with an interactive secondary display 13362, 13364.

In various instances, the processor of a robotic surgical system, such as the robotic surgical systems 13000 (FIG. 4), 13400 (FIG. 5), 13360 (FIG. 6), and/or the surgical hub 13380, 13382, for example, is programmed with pre-approved functions of the robotic surgical system. For example, if a clinician input from the interactive secondary display 13362, 13364 corresponds to a pre-approved function, the robotic surgical system allows for the interactive secondary display 13362, 13364 to control the robotic surgical system and/or does not prohibit the interactive secondary display 13362, 13364 from controlling the robotic surgical system. If a clinician input from the interactive secondary display 13362, 13364 does not correspond to a pre-approved function, the interactive secondary display 13362, 13364 is unable to command the robotic surgical system to perform the desired function. In one instances, a situational awareness module in the robotic hub 13370 and/or the surgical hub 13382 is configured to dictate and/or influence when the interactive secondary display can issue control motions to the robot surgical system.

In various instances, an interactive secondary display 13362, 13364 has control over a portion of the robotic surgical system upon making contact with the portion of the robotic surgical system. For example, when the interactive secondary display 13362, 13364 is brought into contact with the robotic tool 13374, control of the contacted robotic tool 13374 is granted to the interactive secondary display 13362, 13364. A clinician can then utilize a touch-sensitive screen and/or buttons on the interactive secondary display 13362, 13364 to input a command to control movement and/or functionality of the contacted robotic tool 13374. This control scheme allows for a clinician to reposition a robotic arm, reload a robotic tool, and/or otherwise reconfigure the robotic surgical system. In a similar manner as discussed above, the clinician 13371 positioned at the remote command console 13370 of the robotic surgical system can manually override any robot command initiated by the interactive secondary display 13362, 13364.

In one aspect, the robotic surgical system includes a processor and a memory communicatively coupled to the processor, as described herein. The memory stores instructions executable by the processor to receive a first user input from a console and to receive a second user input from a mobile wireless control module for controlling a function of a robotic surgical tool, as described herein.

In various aspects, the present disclosure provides a control circuit to receive a first user input from a console and to receive a second user input from a mobile wireless control module for controlling a function of a robotic surgical tool, as described herein. In various aspects, the present disclosure provides a non-transitory computer readable medium storing computer readable instructions which, when executed, cause a machine to receive a first user input from a console and to receive a second user input from a mobile wireless control module for controlling a function of a robotic surgical tool, as described herein.

A robotic surgical system may include multiple robotic arms that are configured to assist the clinician during a surgical procedure. Each robotic arm may be operable independently of the others. A lack of communication may exist between each of the robotic arms as they are independently operated, which may increase the risk of tissue trauma. For example, in a scenario where one robotic arm is configured to apply a force that is stronger and in a different direction than a force configured to be applied by a second robotic arm, tissue trauma can result. For example, tissue trauma and/or tearing may occur when a first robotic arm applies a strong retracting force to the tissue while a second robotic arm is configured to rigidly hold the tissue in place.

In various instances, one or more sensors are attached to each robotic arm of a robotic surgical system. The one or more sensors are configured to sense a force applied to the surrounding tissue during the operation of the robotic arm. Such forces can include, for example, a holding force, a retracting force, and/or a dragging force. The sensor from each robotic arm is configured to communicate the magnitude and direction of the detected force to a control unit of the robotic surgical system. The control unit is configured to analyze the communicated forces and set limits for maximum loads to avoid causing trauma to the tissue in a surgical site. For example, the control unit may minimize the holding force applied by a first robotic arm if the retracting or dragging force applied by a second robotic arm increases.

Figure 4A:
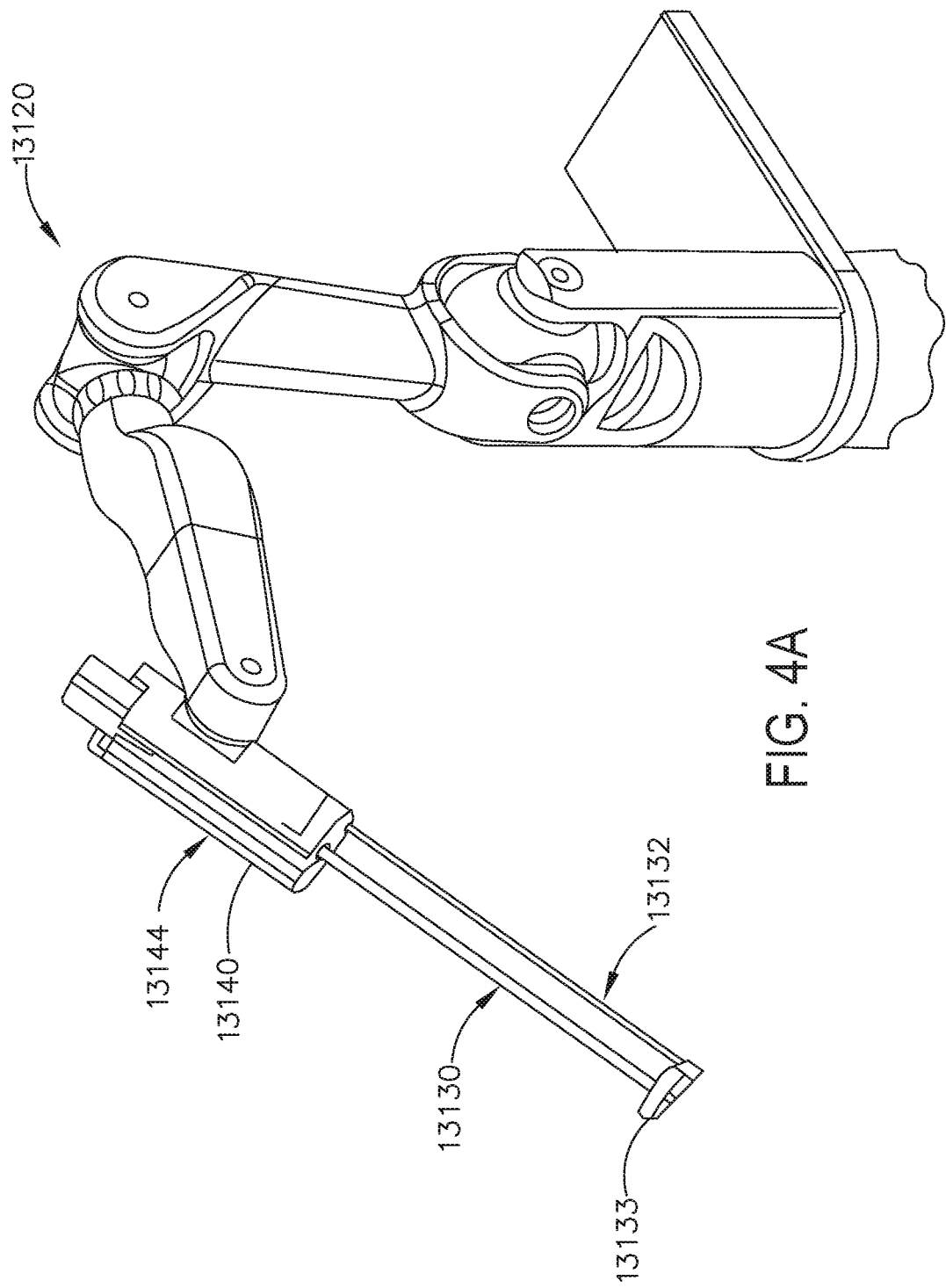
FIG. 4A illustrates another exemplification of a robotic arm and another exemplification of a tool assembly releasably coupled to the robotic arm, according to one aspect of the present disclosure.

FIG. 4A illustrates an exemplification of a robotic arm 13120 and a tool assembly 13130 releasably coupled to the robotic arm 13120. The robotic arm 13120 can support and move the associated tool assembly 13130 along one or more mechanical degrees of freedom (e.g., all six Cartesian degrees of freedom, five or fewer Cartesian degrees of freedom, etc.).

The robotic arm 13120 can include a tool driver 13140 at a distal end of the robotic arm 13120, which can assist with controlling features associated with the tool assembly 13130. The robotic arm 13120 can also include a movable tool guide 13132 that can retract and extend relative to the tool driver 13140. A shaft of the tool assembly 13130 can extend parallel to a threaded shaft of the movable tool guide 13132 and can extend through a distal end feature 13133 (e.g., a ring) of the movable tool guide 13132 and into a patient.

In order to provide a sterile operation area while using the surgical system, a barrier can be placed between the actuating portion of the surgical system (e.g., the robotic arm 13120) and the surgical instruments (e.g., the tool assembly 13130) in the sterile surgical field. A sterile component, such as an instrument sterile adapter (ISA), can also be placed at the connecting interface between the tool assembly 13130 and the robotic arm 13120. The placement of an ISA between the tool assembly 13130 and the robotic arm 13120 can ensure a sterile coupling point for the tool assembly 13130 and the robotic arm 13120. This permits removal of tool assemblies 13130 from the robotic arm 13120 to exchange with other tool assemblies 13130 during the course of a surgery without compromising the sterile surgical field.

The tool assembly 13130 can be loaded from a top side of the tool driver 13140 with the shaft of the tool assembly 13130 being positioned in a shaft-receiving channel 13144 formed along the side of the tool driver 13140, The shaft-receiving channel 13144 allows the shaft, which extends along a central axis of the tool assembly 13130, to extend along a central axis of the tool driver 13140 when the tool assembly 13130 is coupled to the tool driver 13140. In other exemplifications, the shaft can extend through on opening in the tool driver 13140, or the two components can mate in various other configurations.

As discussed above, the robotic surgical system can include one or more robotic arms with each robotic arm having a tool assembly coupled thereto. Each tool assembly can include an end effector that has one or more of a variety of features, such as one or more tools for assisting with performing a surgical procedure. For example, the end effector can include a cutting or boring tool that can be used to perforate or cut through tissue (e.g., create an incision).

Furthermore, some end effectors include one or more sensors that can sense a variety of characteristics associated with either the end effector or the tissue. Each robotic arm and end effector can be controlled by a control system to assist with creating a desired cut or bore and prevent against undesired cutting of tissue. As an alternative to (or in addition to) controlling the robotic arm, it is understood that the control system can control either the tool itself or the tool assembly.

One or more aspects associated with the movement of the robotic arm can be controlled by the control system, such as either a direction or a velocity of movement. For example, when boring through tissue, the robotic arm can be controlled to perform jackhammer-like movements with the cutting tool. Such jackhammer movements can include the robotic arm moving up and down along an axis (e.g., an axis that is approximately perpendicular to the tissue being perforated) in a rapid motion while also advancing the cutting tool in a downward direction towards the tissue to eventually perforate the tissue with the cutting tool (e.g. an ultrasonic blade). While performing such movements in a robotic surgical procedure, not only can it be difficult to see the tissue being perforated to thereby determine a relative position of the cutting tool, but it can also be difficult to determine when the cutting tool has completed perforating the tissue. Such position of the cutting tool relative to the tissue can include the cutting tool approaching or not yet in contact with the tissue, the cutting tool drilling down or cutting into the tissue, and the cutting tool extending through or having perforated the tissue. These positions can be difficult for either a user controlling the robotic arm or the robotic surgical system to determine which can result in potential harm to the patient due to over or under-penetrating the tissue, as well as result in longer procedure times. As such, in order to reduce procedure time and surgical errors, the robotic surgical system includes a control system that communicates with at least one sensor assembly configured to sense a force applied at a distal end of the end effector or cutting tool. The control system can thereby determine and control, based on such sensed forces, one or more appropriate aspects associated with the movement of the robotic arm, such as when boring or cutting into tissue, as will be described in greater detail below.

Although a cutting tool for perforating tissue is described in detail herein, the sensor assembly of the present disclosure that is in communication with the control system can be implemented in any number of robotic surgical systems for detecting any number of a variety of tools and/or end effectors used for performing any number of a variety of procedures without departing from the scope of this disclosure. Furthermore, any number of movements can be performed by the robotic arm to perforate or cut tissue using the robotic surgical system including the sensor assembly and control system described herein and is not limited to the jackhammering or boring of tissue.

FIG. 4A and additional exemplifications are further described in U.S. patent application Ser. No. 15/237,753, entitled CONTROL OF ADVANCEMENT RATE AND APPLICATION FORCE BASED ON MEASURED FORCES, filed Aug. 16, 2016, the entire disclosure of which is incorporated by reference herein.

The entire disclosures of:
U.S. Pat. No. 9,072,535, filed May 27, 2011, entitled SURGICAL STAPLING INSTRUMENTS WITH ROTATABLE STAPLE DEPLOYMENT ARRANGEMENTS, which issued Jul. 7, 2015;
U.S. Pat. No. 9,072,536, filed Jun. 28, 2012, entitled DIFFERENTIAL LOCKING ARRANGEMENTS FOR ROTARY POWERED SURGICAL INSTRUMENTS, which issued Jul. 7, 2015;
U.S. Pat. No. 9,204,879, filed Jun. 28, 2012, entitled FLEXIBLE DRIVE MEMBER, which issued on Dec. 8, 2015;
U.S. Pat. No. 9,561,038, filed Jun. 28, 2012, entitled INTERCHANGEABLE CLIP APPLIER, which issued on Feb. 7, 2017;
U.S. Pat. No. 9,757,128, filed Sep. 5, 2014, entitled MULTIPLE SENSORS WITH ONE SENSOR AFFECTING A SECOND SENSOR'S OUTPUT OR INTERPRETATION, which issued on Sep. 12, 2017;
U.S. patent application Ser. No. 14/640,935, entitled OVERLAID MULTI SENSOR RADIO FREQUENCY (RF) ELECTRODE SYSTEM TO MEASURE TISSUE COMPRESSION, filed Mar. 6, 2015, now U.S. Patent Application Publication No. 2016/0256071;
U.S. patent application Ser. No. 15/382,238, entitled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Patent Application Publication No. 2017/0202591; and
U.S. patent application Ser. No. 15/237,753, entitled CONTROL OF ADVANCEMENT RATE AND APPLICATION FORCE BASED ON MEASURED FORCES, filed Aug. 16, 2016 are hereby incorporated by reference herein in their respective entireties.

The surgical devices, systems, and methods disclosed herein can be implemented with a variety of different robotic surgical systems and surgical devices. Surgical devices include robotic surgical tools and handheld surgical instruments. The reader will readily appreciate that certain devices, systems, and methods disclosed herein are not limited to applications within a robotic surgical system. For example, certain systems, devices, and methods for communicating, detecting, and/or control a surgical device can be implemented without a robotic surgical system.

Surgical Network

Figure 8:
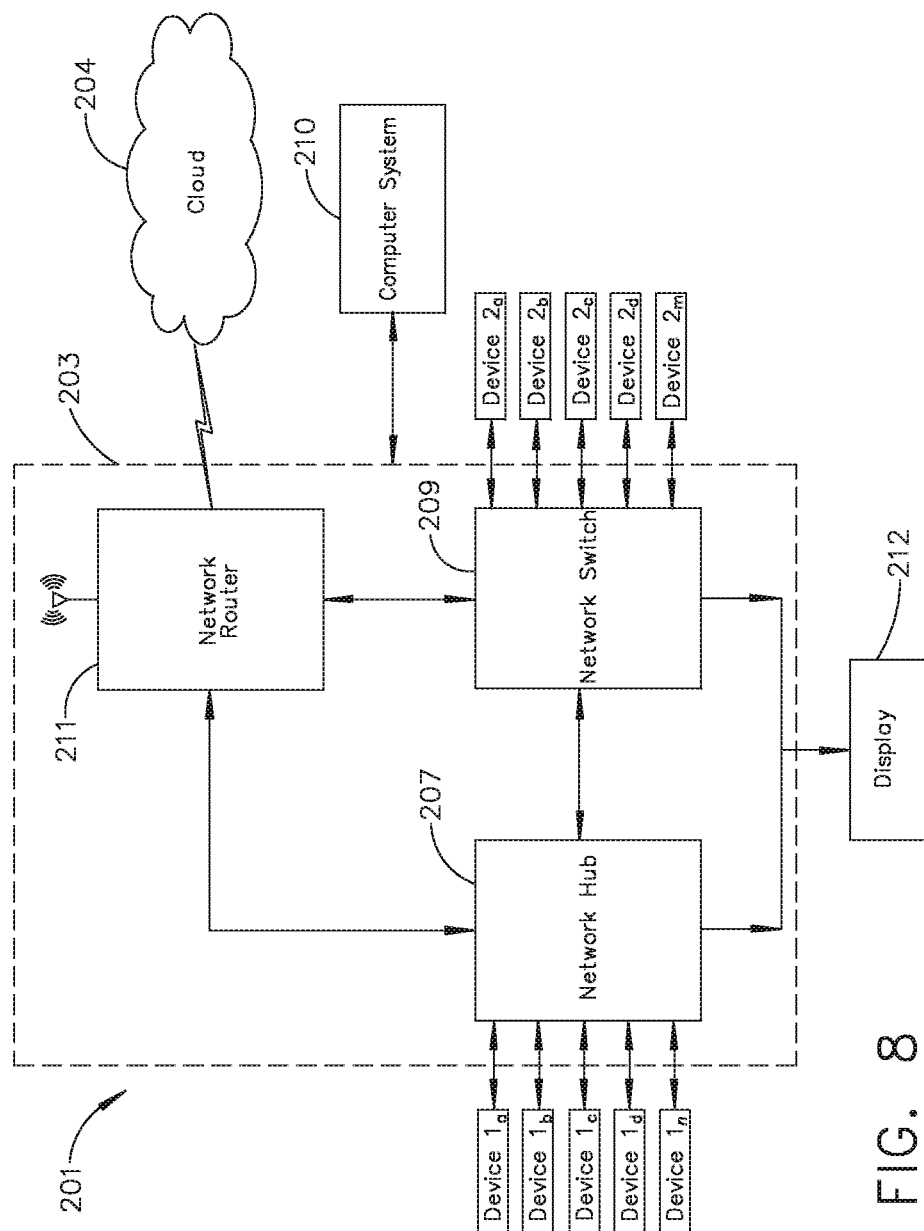
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/internet protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
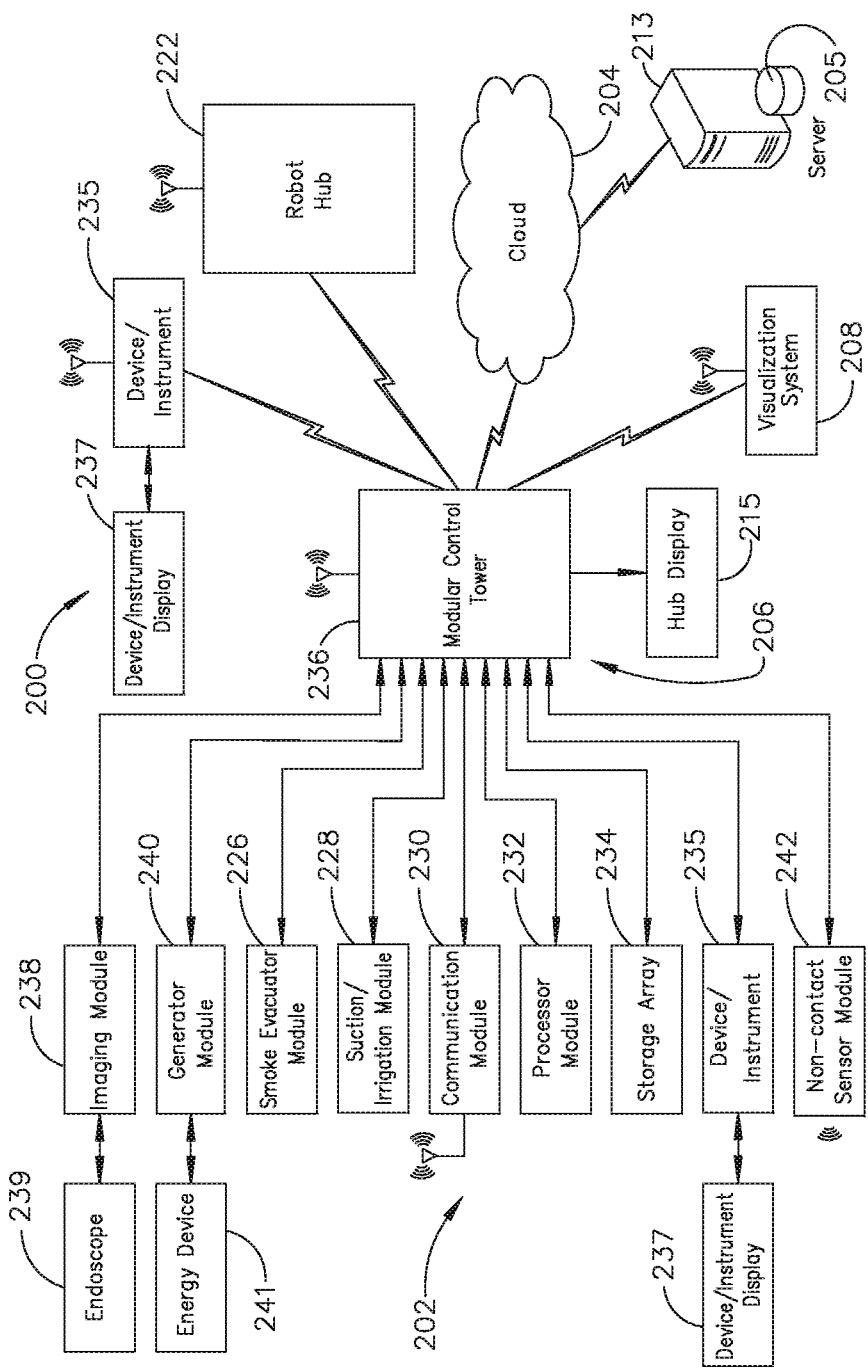
FIG. 9 illustrates a computer-implemented interactive surgical system, in accordance with at least one aspect of the present disclosure.
Figure 10:
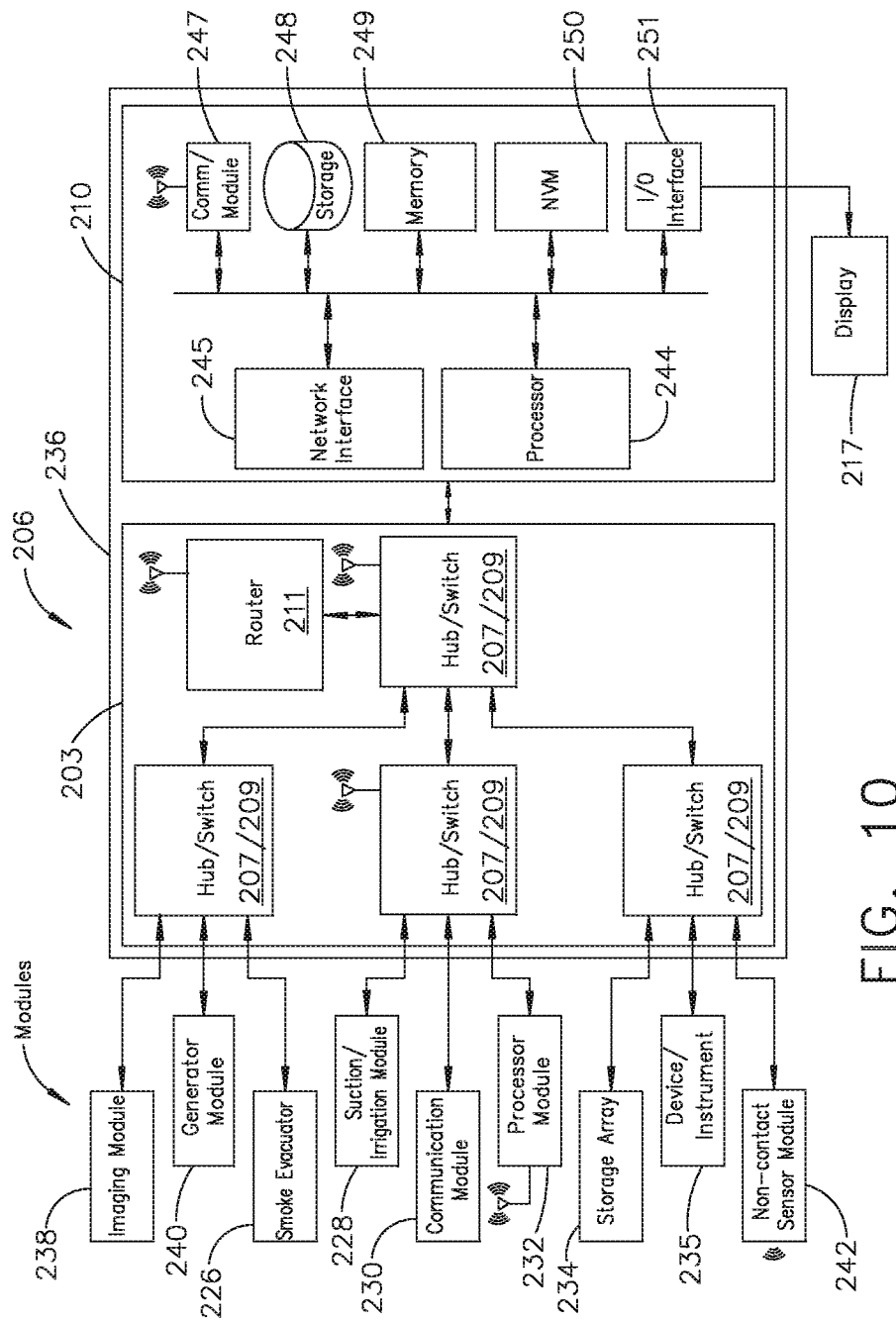
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208.

The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, the disclosure of which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
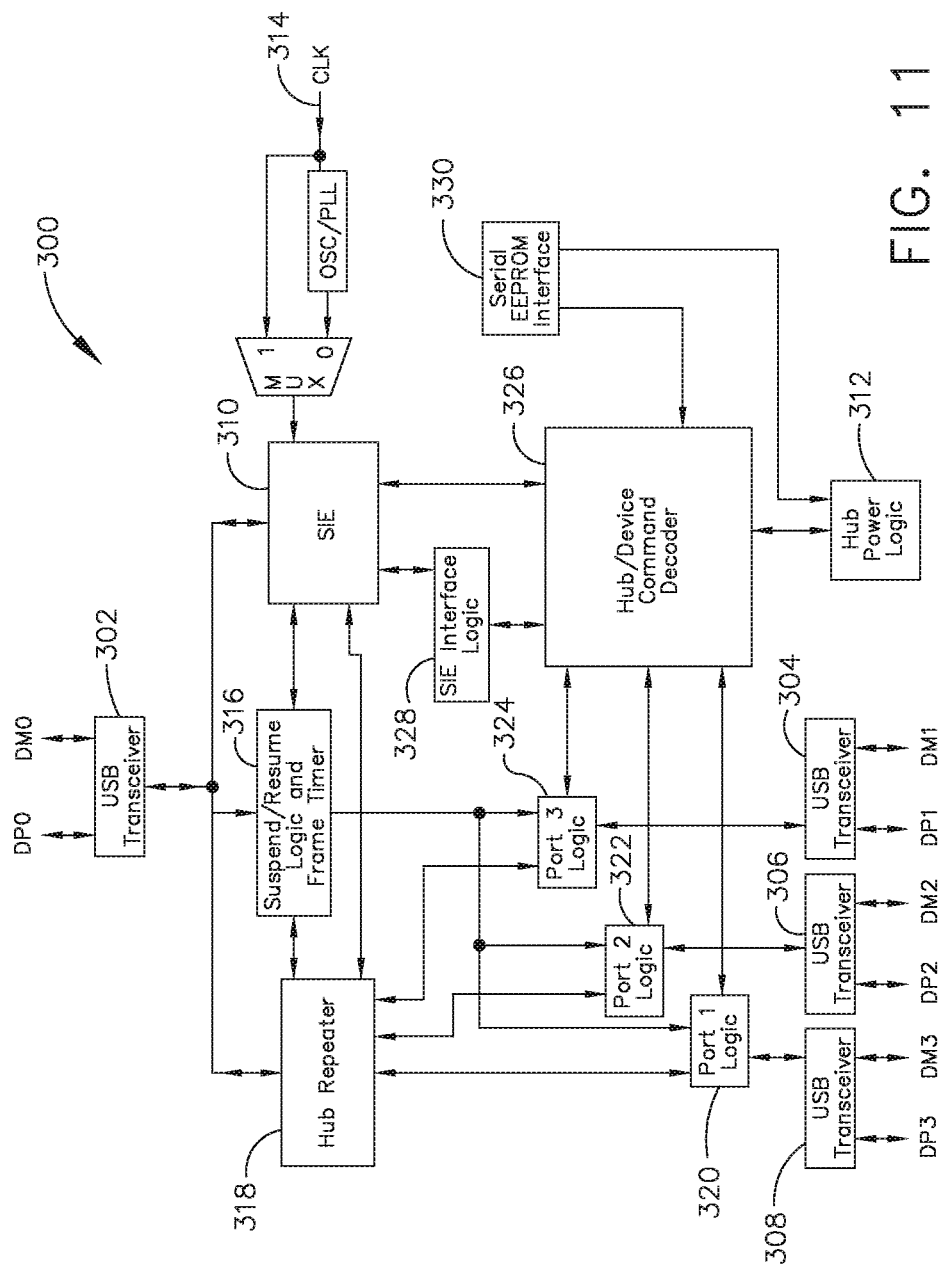
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
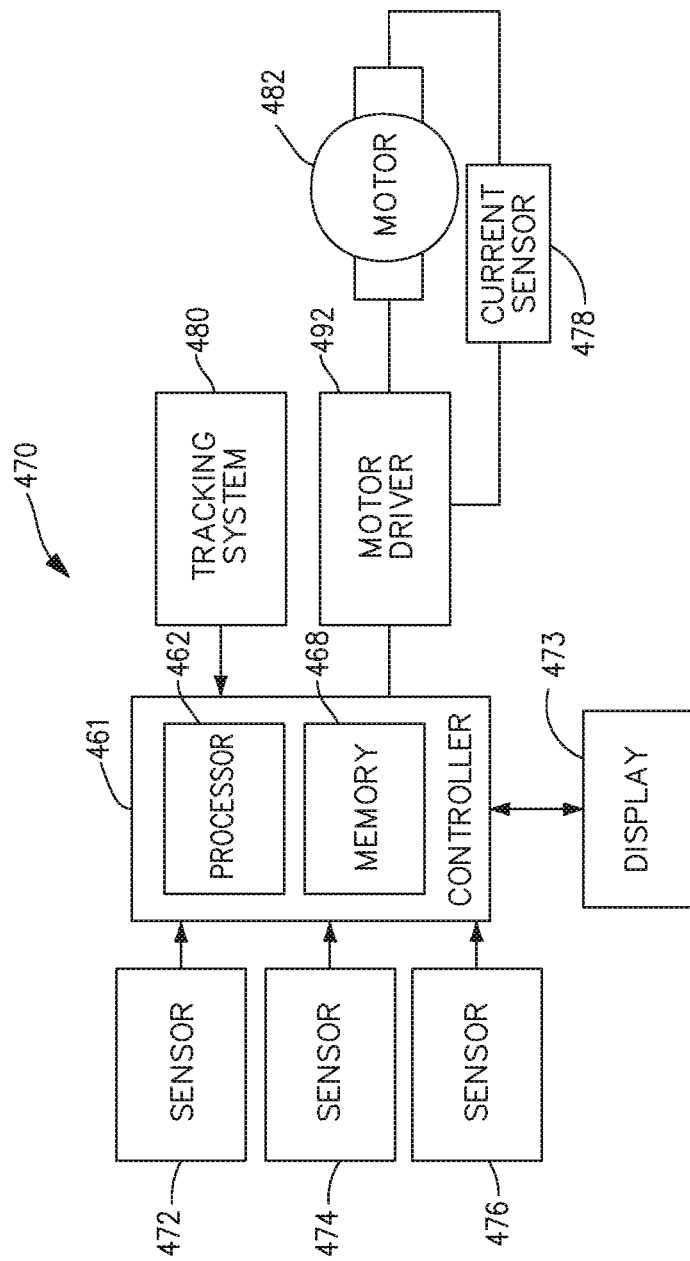
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
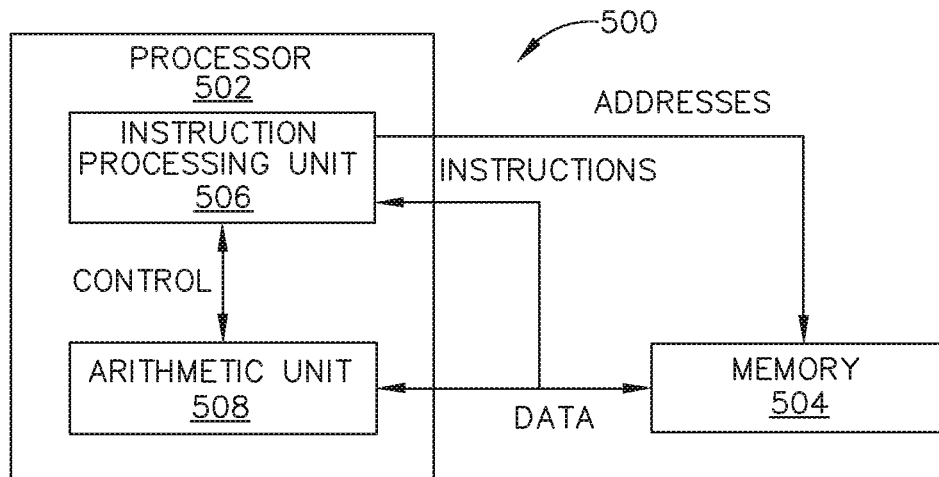
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
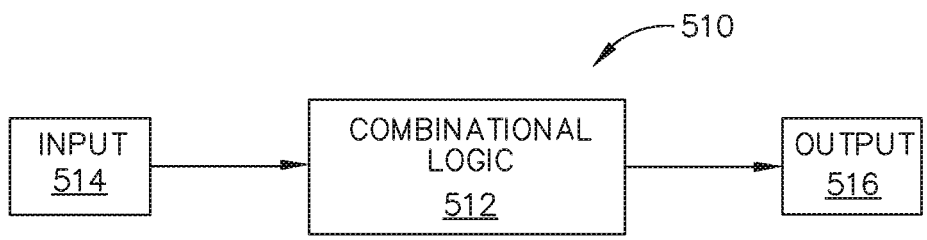
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
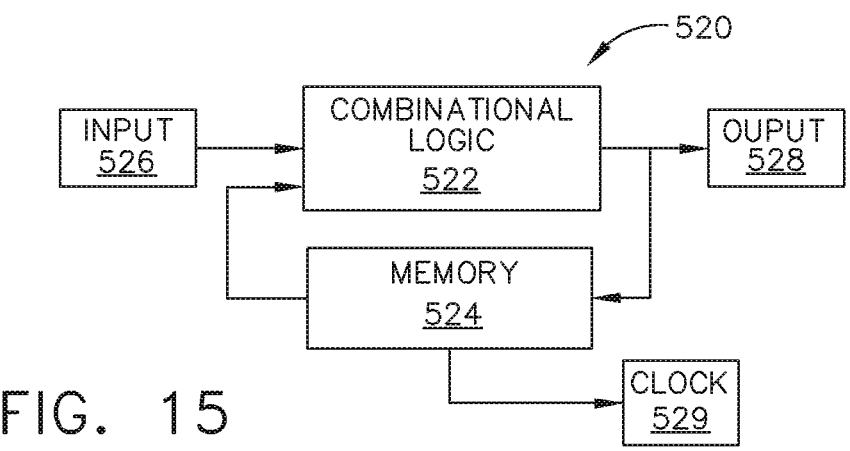
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
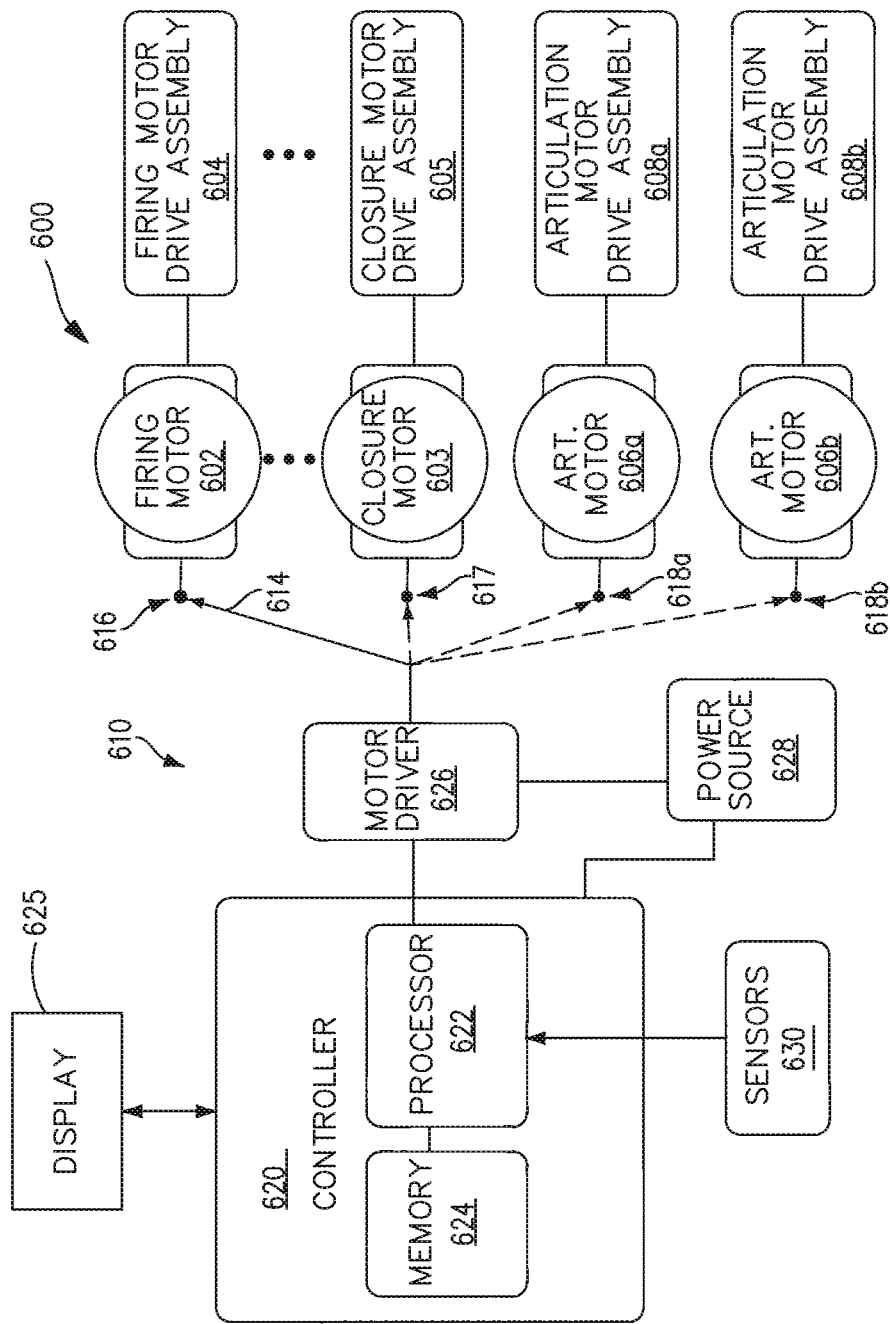
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail herein below.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
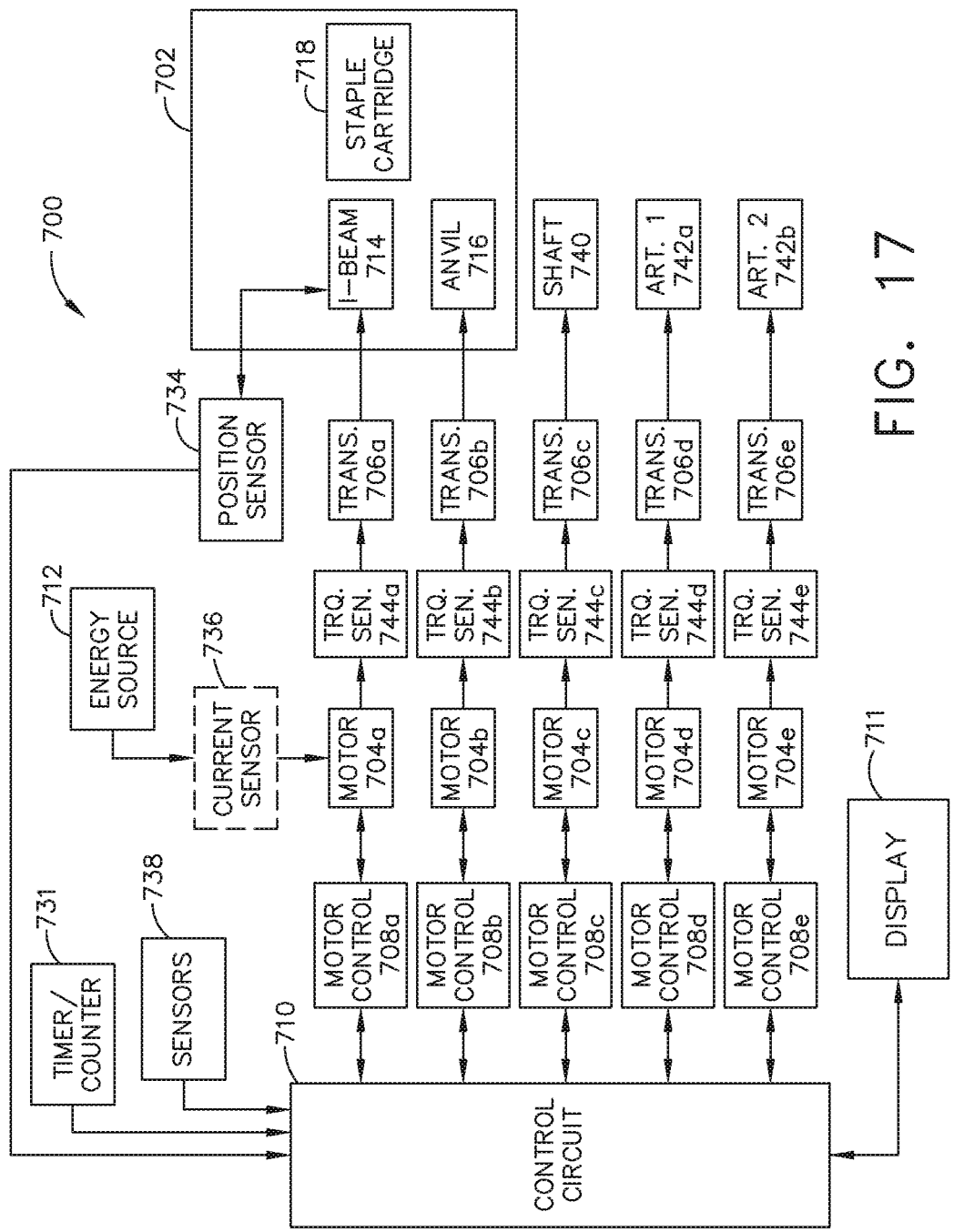
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members.

The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702 ±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORD IC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
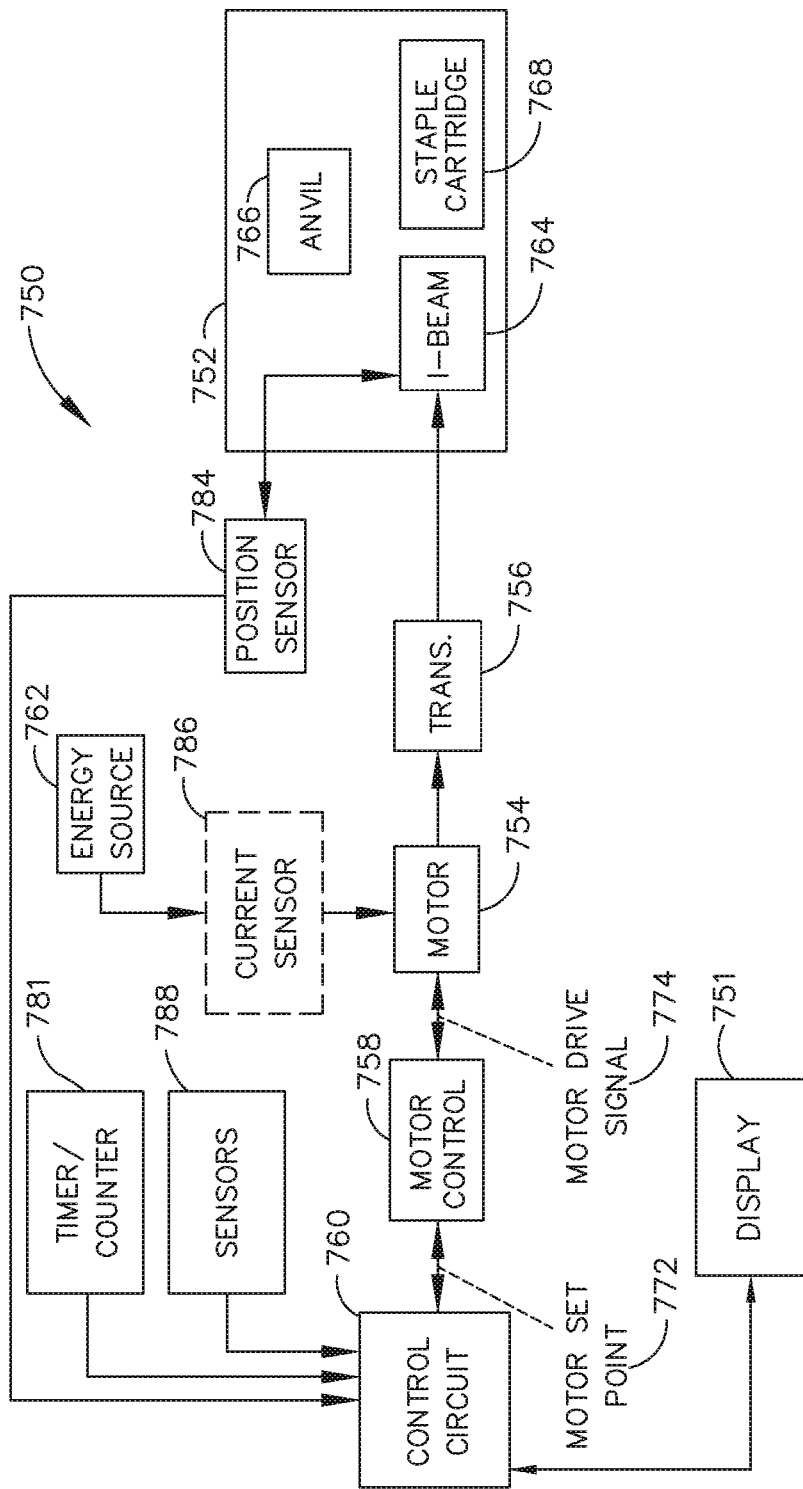
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as a drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
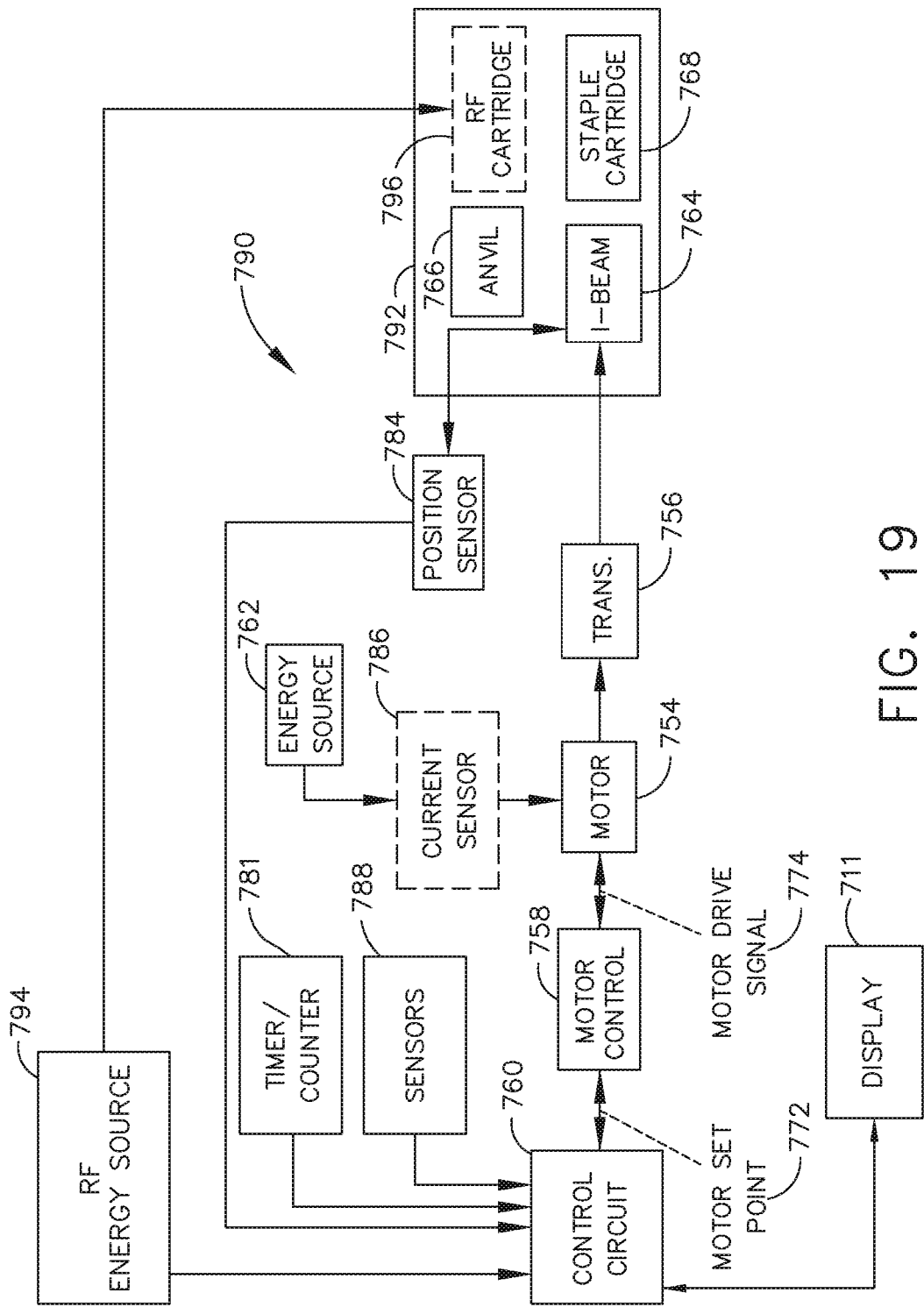
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Figure 20:
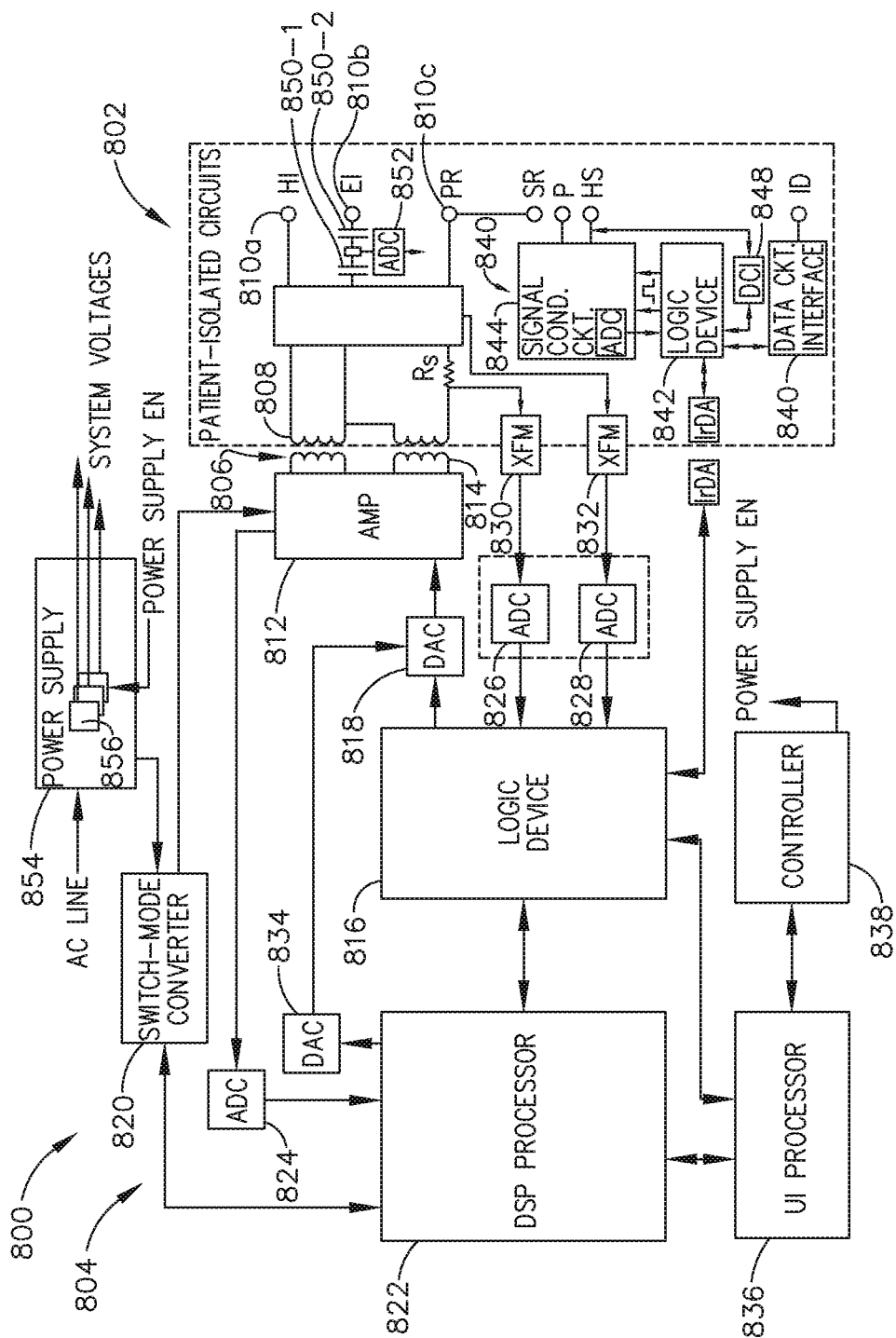
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, Mass., for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, Calif., for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
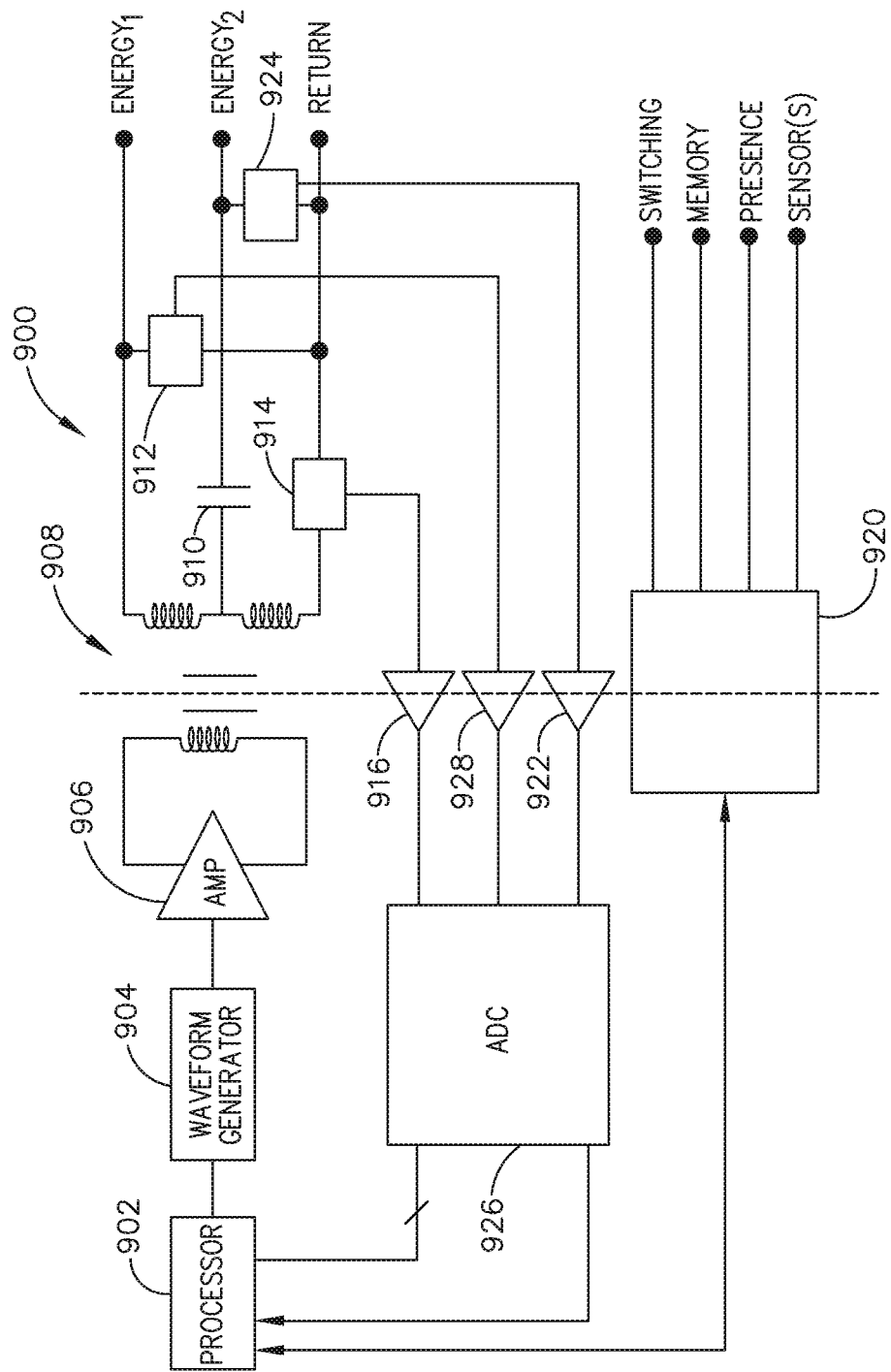
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 21). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Robotic surgical systems can be used in minimally invasive medical procedures. During such medical procedures, a patient can be placed on a platform adjacent to a robotic surgical system, and a surgeon can be positioned at a console that is remote from the platform and/or from the robot. For example, the surgeon can be positioned outside the sterile field that surrounds the surgical site. The surgeon provides input to a user interface via an input device at the console to manipulate a surgical tool coupled to an arm of the robotic system. The input device can be a mechanical input devices such as control handles or joysticks, for example, or contactless input devices such as optical gesture sensors, for example.

The robotic surgical system can include a robot tower supporting one or more robotic arms. At least one surgical tool (e.g. an end effector and/or endoscope) can be mounted to the robotic arm. The surgical tool(s) can be configured to articulate relative to the respective robotic arm via an articulating wrist assembly and/or to translate relative to the robotic arm via a linear slide mechanism, for example. During the surgical procedure, the surgical tool can be inserted into a small incision in a patient via a cannula or trocar, for example, or into a natural orifice of the patient to position the distal end of the surgical tool at the surgical site within the body of the patient. Additionally or alternatively, the robotic surgical system can be employed in an open surgical procedure in certain instances.

Figure 22:
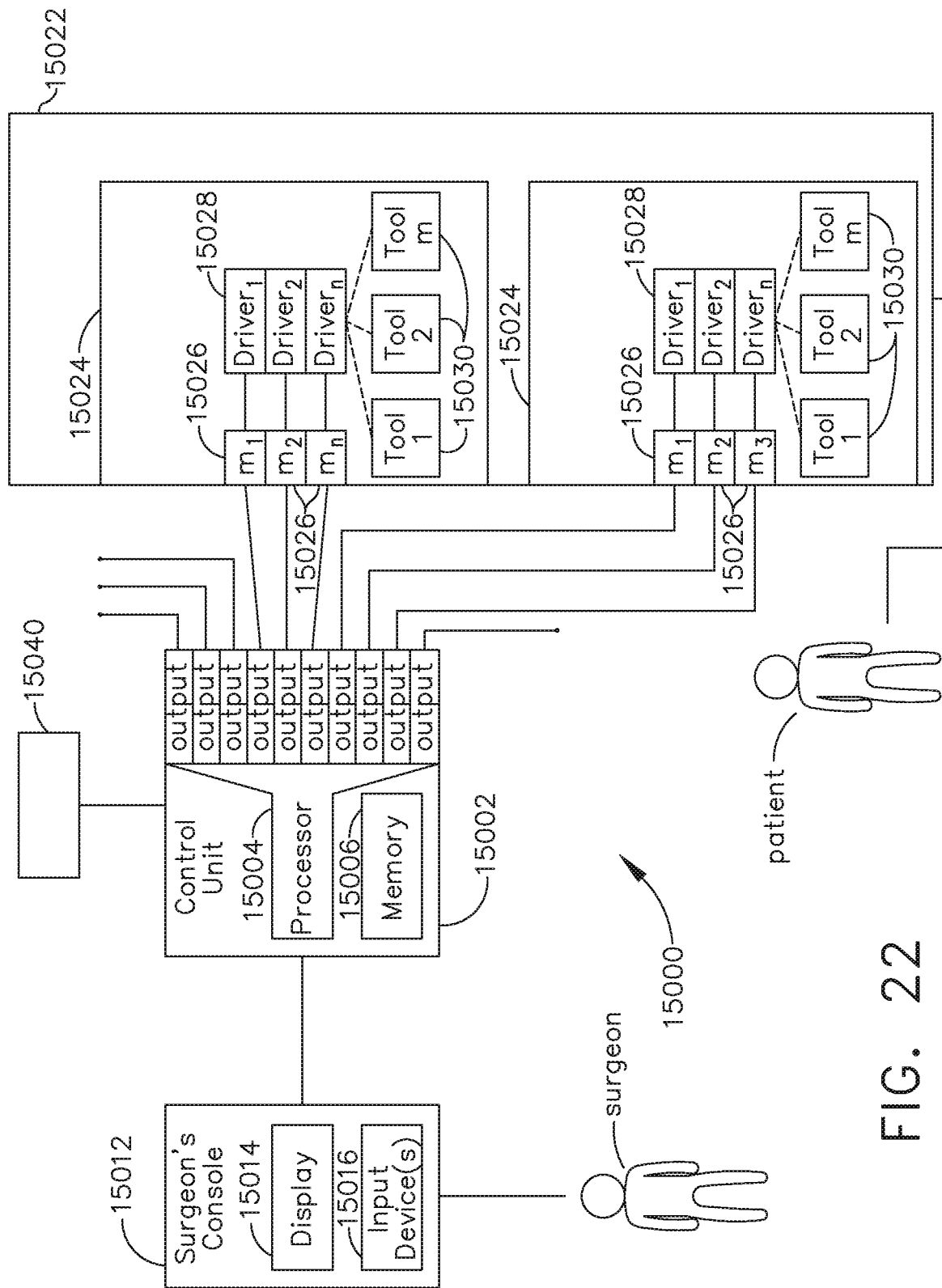
FIG. 22 is a schematic of a robotic surgical system, in accordance with one aspect of the present disclosure.

A schematic of a robotic surgical system 15000 is depicted in FIG. 22. The robotic surgical system 15000 includes a central control unit 15002, a surgeon's console 15012, a robot 15022 including one or more robotic arms 15024, and a primary display 15040 operably coupled to the control unit 15002. The surgeon's console 15012 includes a display 15014 and at least one manual input device 15016 (e.g., switches, buttons, touch screens, joysticks, gimbals, etc.) that allow the surgeon to telemanipulate the robotic arms 15024 of the robot 15022. The reader will appreciate that additional and alternative input devices can be employed.

The central control unit 15002 includes a processor 15004 operably coupled to a memory 15006. The processor 15004 includes a plurality of inputs and outputs for interfacing with the components of the robotic surgical system 15000. The processor 15004 can be configured to receive input signals and/or generate output signals to control one or more of the various components (e.g., one or more motors, sensors, and/or displays) of the robotic surgical system 15000. The output signals can include, and/or can be based upon, algorithmic instructions which may be pre-programmed and/or input by the surgeon or another clinician. The processor 15004 can be configured to accept a plurality of inputs from a user, such as the surgeon at the console 15012, and/or may interface with a remote system. The memory

15006 can be directly and/or indirectly coupled to the processor 15004 to store instructions and/or databases.

The robot 15022 includes one or more robotic arms 15024. Each robotic arm 15024 includes one or more motors 15026 and each motor 15026 is coupled to one or more motor drivers 15028. For example, the motors 15026, which can be assigned to different drivers and/or mechanisms, can be housed in a carriage assembly or housing. In certain instances, a transmission intermediate a motor 15026 and one or more drivers 15028 can permit coupling and decoupling of the motor 15026 to one or more drivers 15028. The drivers 15028 can be configured to implement one or more surgical functions. For example, one or more drivers 15028 can be tasked with moving a robotic arm 15024 by rotating the robotic arm 15024 and/or a linkage and/or joint thereof. Additionally, one or more drivers 15028 can be coupled to a surgical tool 15030 and can implement articulating, rotating, clamping, sealing, stapling, energizing, firing, cutting, and/or opening, for example. In certain instances, the surgical tools 15030 can be interchangeable and/or replaceable. Examples of robotic surgical systems and surgical tools are further described herein.

The reader will readily appreciate that the computer-implemented interactive surgical system 100 (FIG. 1) and the computer-implemented interactive surgical system 200 (FIG. 9) can incorporate the robotic surgical system 15000. Additionally or alternatively, the robotic surgical system 15000 can include various features and/or components of the computer-implemented interactive surgical systems 100 and 200.

In one exemplification, the robotic surgical system 15000 can encompass the robotic system 110 (FIG. 2), which includes the surgeon's console 118, the surgical robot 120, and the robotic hub 122. Additionally or alternatively, the robotic surgical system 15000 can communicate with another hub, such as the surgical hub 106, for example. In one instance, the robotic surgical system 15000 can be incorporated into a surgical system, such as the computer-implemented interactive surgical system 100 (FIG. 1) or the computer-implemented interactive surgical system 200 (FIG. 9), for example. In such instances, the robotic surgical system 15000 may interact with the cloud 104 or the cloud 204, respectively, and the surgical hub 106 or the surgical hub 206, respectively. In certain instances, a robotic hub or a surgical hub can include the central control unit 15002 and/or the central control unit 15002 can communicate with a cloud. In other instances, a surgical hub can embody a discrete unit that is separate from the central control unit 15002 and which can communicate with the central control unit 15002.

Detachable Surgical Device Motor Pack

As previously disclosed above with respect to FIGS. 4 and 4A, a surgical environment may incorporate a robotic surgical system. The robotic surgical system 13000 includes robotic arms 13002, 13003, a control device 13004, and a console 13005 coupled to the control device 13004. As illustrated in FIG. 4, the surgical system 13000 is configured for use on a patient 13013 lying on a patient table 13012 for performance of a minimally invasive surgical operation. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003. Each of the robotic arms 13002, 13003 is made up of a plurality of members connected through joints and includes a surgical assembly 13010 connected to a distal end of a corresponding robotic arm 13002, 13003.

The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008. The control device 13004 may also be configured to regulate movement of the robotic arms 13002, 13003 and/or of the drives.

The control device 13004 may control a plurality of motors (for example, Motor I . . . n) with each motor configured to drive a pushing or a pulling of one or more cables, such as cables coupled to the end effector 13023 of the surgical instrument 13020. In use, as these cables are pushed and/or pulled, the one or more cables affect operation and/or movement of the end effector 13023. The control device 13004 coordinates the activation of the various motors to coordinate a pushing or a pulling motion of one or more cables in order to coordinate an operation and/or movement of one or more end effectors 13023.

Moreover, a plurality of surgical devices can be used in certain robotic surgical procedures. For example, a robotic surgical system can use one or more surgical tools during the surgical procedure. Additionally, one or more handheld instruments can also be used during the surgical procedure. In some instances, more than one surgeon may be required during a surgical procedure and it may be difficult to coordinate separate tasks among the surgeons. Alternatively, a robotic system may not have sufficient arms to carry out multiple tasks. Such a handheld device may also have the capability of using multiple detachable end effectors or surgical tools, and may also have other modular capabilities. Examples of such a modular hand-held surgical instrument may be found in U.S. patent application Ser. No. 15/382,285, titled MODULAR BATTERY POWERED HAND-HELD SURGICAL INSTRUMENT WITH VOLTAGE SAG RESISTANT BATTERY PACK and filed Dec. 16, 2016, the disclosure of which is herein incorporated by reference in its entirety and for all purposes.

For cost effectiveness, it may be useful to have the modular end effectors or surgical tools usable by the hand-held device also to be employed by the robotic device. Thus, a single modular end effector or surgical tool may be installed in either the modular hand-held device or the robotic device. In such cases, all electrical and mechanical interfaces for the modular end effectors must be consistent between the hand-held and the robotic platforms. In some aspects, this consistency may be obtained by using a detachable surgical device motor pack. This detachable motor pack may be installed on an end of a robotic surgical device arm or within a housing of the modular hand-held device. The modular end effector may then mate with the detachable motor pack in either of the hand-held instrument or the robotic instrument. Some exemplary aspects of a detachable motor pack may be found in U.S. Pat. No. 8,912,746 titled SURGICAL INSTRUMENT MOTOR PACK LATCH filed Oct. 26, 2012, the disclosure of which is herein incorporated by reference in its entirety and for all purposes.

The detachable motor pack may comprise a housing, a plurality of motors retained within the housing, a controller configured to control one or more operations of the plurality of motors, a first interface portion configured to releasably attach to a hand-held surgical instrument and to a robotic surgical instrument, and a second interface portion configured to releasably attach to a first surgical end effector of the hand-held surgical instrument and to a second surgical end effector of the robotic surgical instrument. In some aspects, the end effector of the hand-held surgical instrument may be the same as the end effector of the robotic surgical instrument. In other aspects, the end effector of the hand-held surgical instrument may differ from the end effector of the robotic surgical instrument.

The first interface portion of the detachable motor pack may comprise mechanical and electrical interface components that, when releasably attached to the hand-held surgical instrument, are configured to operate with a handle assembly interface. The handle assembly interface may communicate mechanical, electrical, or both mechanical and electrical outputs to control the detachable motor pack operations. Mechanical outputs may be derived from one or more buttons, slides, triggers, or other mechanically operated components to direct the operation of the detachable motor pack. Electrical outputs to control the detachable motor pack operations may include electrical signals to the detachable motor pack controller. The detachable motor pack control may also provide status and operational signals in return to the handle assembly interface to provide status information to controller electronics in the hand-held surgical device.

The first interface portion of the detachable motor pack may comprise mechanical and electrical interface components that, when releasably attached to the robotic surgical instrument, are configured to operate with a robotic arm interface. In some aspects, the robotic arm interface may be part of the electrical drives connected to the robotic control device. In some aspects, the robotic arm interface may be configured to conduct one or more drive signals or one or more control signals to the first interface portion of the detachable motor pack. The robotic arm interface may be in electrical and data communication with robotic system control device. Electrical outputs from the robotic arm interface may control the detachable motor pack operations and may include electrical signals to control the detachable motor pack controller. In some aspects, the control device may control the plurality of motors disposed within the detachable motor pack, with each motor configured to drive a pushing or a pulling of one or more cables, such as cables coupled to the modular end effector. The detachable motor pack control may also provide status and operational signals to the robotic surgical system control device to provide status information to the robotic system.

The second interface portion of the detachable motor pack is configured to mate with an interface of the modular end effector or surgical tool. The second interface portion may include mechanical components configured to drive the mechanical drive portions of the modular end effector. The drive portions of the modular end effector may control a variety of mechanical functions of the end effector including, without limitation, a grasping jaw, a cutting implement, or a stapling anvil. Each mechanical component of the second interface portion may be mechanically coupled directly to a motor shaft, or to one or more gears comprising a mechanical drive train. The second interface portion may include electrical components configured to deliver electrical energy to the modular end effector. Such energy may be used to power one or more RF electrodes for sealing or cutting operations, or the energy may be delivered to a high frequency component such as a piezoelectric stack used by an ultrasonic cutter or tissue sealer. The electrical components of the second interface may also be used to receive sensor information from the end effector. Such sensor information may be relayed to control components of either the hand-held device or the robotic device. Sensor data received from the end-effector or surgical tool may include, without limitation, limit signals indicating that a desired mechanical motion has reached an end of travel for safe operation.

The first interface portion may incorporate features designed to secure the detachable motor pack to either the robotic device or the hand-held device. Such features may include latching features, such as bolt holes or hooks, and alignment features such as dove-tails or alignment pins. The second interface portion may incorporate features designed to secure the detachable motor pack to a modular end effector or surgical tool. The features for securing the detachable motor pack to either the robotic device or the handheld device may be the same as or different from the features for securing the detachable motor pack to the modular end effectors. In one aspect, the features for securing the detachable motor pack to the end effectors and to the hand-held surgical device or robotic surgical device may be included in either the first interface portion or the second interface portion. In another aspect, the features for securing the detachable motor pack to the end effectors and to the hand-held surgical device or robotic surgical device may be incorporated into the motor pack housing. It is understood that the features for securing the detachable motor pack to the end effectors and to the hand-held surgical device or robotic surgical device may be incorporated in both the housing and in the first and second interface portions.

As disclosed above, the detachable motor pack includes a plurality of motors. The detachable motor pack may include one, two, three, four, or more motors as required to drive the functions of the end effectors. Such motors may include any type of motor appropriate for the use with the detachable end effectors. Examples of such motors may include, without limitation, DC brushed motors, DC brushless motors, servo motors, direct drive motors, and stepper motors. Such motors may also incorporate components capable of sensing the rotational position of the motor shaft such as optical encoders, magnetic encoders, or resistive encoders. The encoders may be incremental or absolute. The detachable motor pack may also include electronics required to power the encoders and transmit positional and velocity data obtained from the encoders. In this manner, the detachable motor pack may provide motor positional and velocity data to the platform to which it is attached (the hand-held device or the robotic device) via the first interface portion. The motors may be mechanically linked to one or more gears or drive trains. The motors may be mechanically coupled to the mechanical components of the second interface portion. In this manner, the motors of the detachable motor pack may be able to drive the mechanical components of the detachable end-effectors or surgical tools when the end-effectors are detachably linked to the motor pack.

The detachable motor pack may also include a controller. The controller may comprise any one or more digital, analog, mixed analog-digital, and integrated circuit components. The controller may further include a processor unit, one or more dynamic memory components, one or more static memory components, and one or more interface components. The static memory components may store instructions, that when executed by the processor, will cause the processor to direct the motion of the plurality of motors.

The controller interface components may include input components and output components. In one aspect, the controller input components may be used by the controller to receive instructions for the operation of the detachable motor pack from the instrument platform (either the hand-held device or the robotic device). In one non-limiting example, the controller may be configured to receive identification information from the surgical platform (either the hand-held device or the robotic device). In some aspects, the detachable motor pack may have independent usage configurations depending on whether it is attached to the robotic device or the hand-held device. The motor pack may have different or fewer functions when attached to the hand-held device than when used with the robot tool driver. In one non-limiting example, functionality changes may include changing the use of a multi-axis articulating surgical tool shaft from multi-axis articulation (for the robotic platform) to single axis articulation (for the hand-held surgical device). The multi-axis articulation of the end-effector may result in more robust independently controllable jaw motions than the single-axis articulation. In another non-limiting example, the instrument platform may provide instructions to move a motor associated with a grasping jaw of an end-effector to a certain position. It may be recognized that the use of a detachable motor pack would permit the platforms to have the modular capability regarding the type of surgical tool used at any time along with the plasticity of how the surgical tool is controlled by each platform.

The input components may also receive data from the motor encoders to allow the processor to properly drive the motors based on their speed and rotary position. The input components may also receive data from sensors on the detachable end-effectors (via the second motor pack interface portion). Such sensor data may also be used to control the motion of the motors. In one non-limiting example, limit switch sensor data may be provided by the end-effectors to notify the controller that a mechanical component on the end-effector has attained a limiting position beyond which it may not safely move, for example a tissue grasping jaw. The input components may also receive device identifying information from the detachable end-effectors. Such identifying information may be used by the controller to associate one of the plurality of motors with a single mechanical activation of the end-effector (such as a grasping jaw). As one non-limiting example, the identifying information from an RF tissue sealing device may be used by the motor pack controller to associate a first motor with a grasping jaw motion, and a second motor with a sliding knife motion.

The controller output interface components may be used to direct the rotary action of the plurality of motors. For example, the output interface components may control the action of the drive electronics for powering the motor windings. The output interface components may also be used to transmit status data to the surgical device platform (the hand-held device or the robotic device). Such status data may relate to the position, direction, and/or velocity of the plurality of motors. The status data may also provide error information, for example that one of the motors is not responsive. The status data may also provide information regarding the state of the coupling of the motor pack first interface portion with the surgical platform (the hand-held device or robotic device) or the state of coupling of the detachable end-effector with the second interface portion. Such information may be useful to determine that the detachable motor pack is properly affixed to the surgical platform or that the end-effector is properly affixed to the motor pack.

In addition to the disclosure above, additional configurations related to the use of the detachable motor pack with a hand-held surgical device may be further described. In one aspect, the hand-held surgical tool may be configured to accept a sterile barrier between a handle component and the detachable motor pack. Accordingly, sterility of the handle component may be maintained while the detachable motor pack is changed. In another aspect, the end-effector or surgical tool may be detachably mounted on the hand-held device frame directly while the detachable motor pack is inserted or exchanged. In yet another aspect, the detachable end-effector or surgical tool may transmit identifying information or operational parameters to the hand-held device controller. Such information or parameter transfer may be effected either directly to the hand-held device controller or indirectly via the interfaces of the detachable motor pack. In this manner, the operation of the detachable end-effector or surgical tool may be controlled by a combination of instructions received from one or more of the hand-held device controller and the motor pack controller.

Additional aspects of the detachable motor pack are further disclosed herein.

In one aspect, the detachable motor pack may include a user display unit, in which the controller is configured to control the user display unit. The display unit may display information related to the velocity and/or position of each of the motors. The display unit may further display fault information. Non-limiting examples of fault information may include mis-alignment of the motor pack with an interface on the surgical platform (hand-held device or robotic device), mis-alignment of the detachable end-effector with the motor pack, or fault data related to malfunctions of the motors. The display unit may additionally display identification information received by the motor pack from the end-effector.

In another aspect, the detachable motor pack may further comprise one or more electrical contacts configured to source electrical signals to one or more mating electrical contacts of the hand-held surgical instrument thereby providing the data to a user display unit of the hand-held surgical instrument.

The electrical contacts may form part of the electrical components of the first interface portion of the motor pack. Such information may include, without limitation, identification information from the end-effector, motor operation information (velocity and position) of the motors, and fault information as disclosed above.

In another aspect, the controller of the motor pack may be configured to control a first set of operations of the plurality of motors when the detachable motor pack is releasably attached to the hand-held surgical instrument, and to control a second set of operations of the plurality of motors when the detachable motor pack is releasably attached to the robotic surgical instrument.

In yet another aspect, the controller of the detachable motor pack may be configured to receive one or more operating parameters from a first surgical tool, such as a first detachable end-effector, and a second surgical tool such as a second detachable end-effector. The detachable motor pack controller may be configured to control the first set of operations based on the one or more operating parameters received from the first surgical tool or end-effector and the controller may be configured to control the second set of operations based on the one or more operating parameters received from the second surgical tool or end effector.

FIGS. 23A-25 depict a non-limiting example of a detachable motor pack that may be used in concert with an exemplary detachable surgical tool.

Figure 23A:
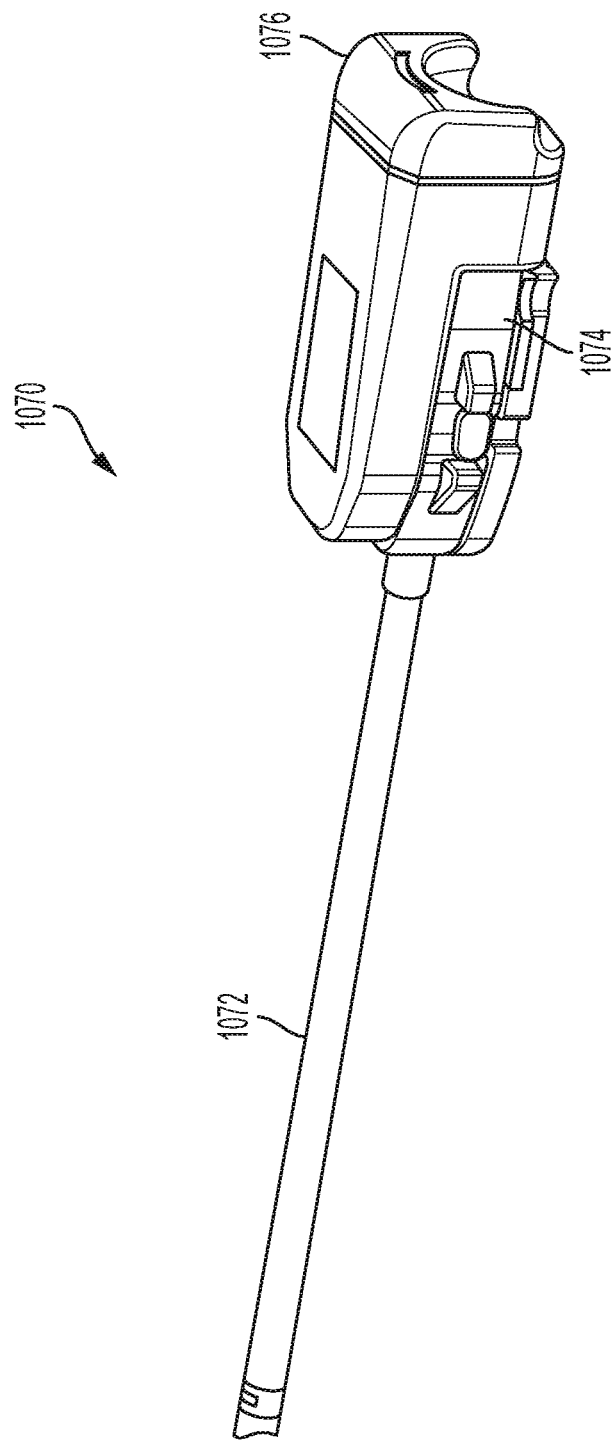
FIG. 23A is a perspective view of a detachable motor pack is mounted to a proximal surgical tool interface, in accordance with at least one aspect of the present disclosure.

FIG. 23A depicts an aspect of a surgical tool/detachable motor pack assembly 1070. The surgical tool/detachable motor pack assembly 1070 includes an elongate surgical instrument shaft 1072 supporting an end effector (not shown) at a distal end of the instrument shaft 1072, a proximal surgical tool interface 1074 supporting the proximal end of the instrument shaft 1072, and a detachable motor pack 1076 mounted and latched to the proximal surgical tool interface 1074. The motor pack 1076 includes electric motors that are drivingly coupled with drivable features of the end effector.

Figure 23B:
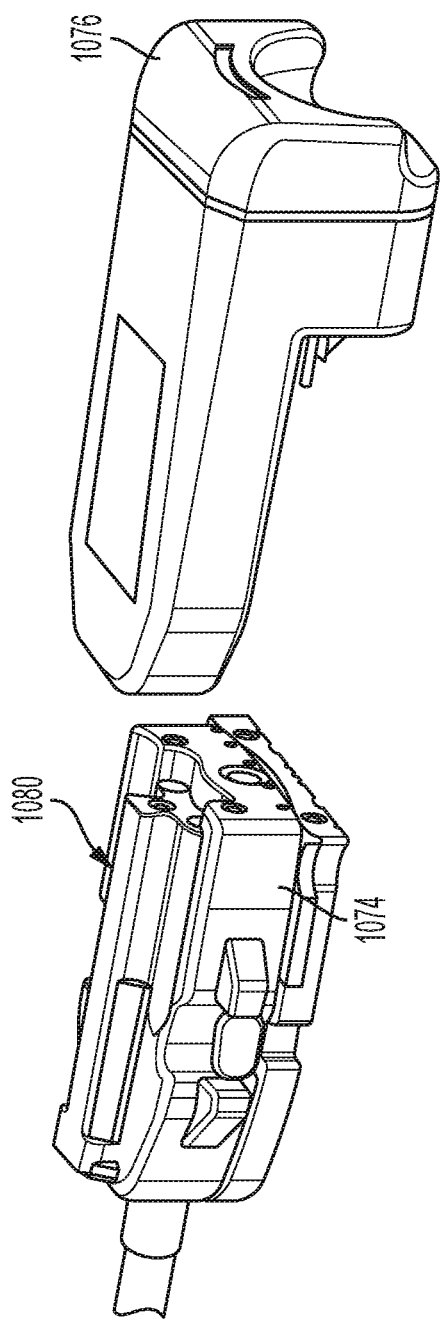
FIG. 23B is a perspective view of the detachable motor pack of FIG. 6A separated from the proximal surgical tool interface.

FIG. 23B shows the motor pack 1076 separated from the proximal surgical tool interface 1074. The top of the proximal surgical tool interface 1074 includes a longitudinally-oriented dovetail alignment feature 1080 that interfaces with a complementarily-shaped dovetail alignment feature of the motor pack 1076 to provide for sliding engagement between the motor pack 1076 and the proximal surgical tool interface 1074 about a longitudinally-oriented engagement axis.

Figure 24:
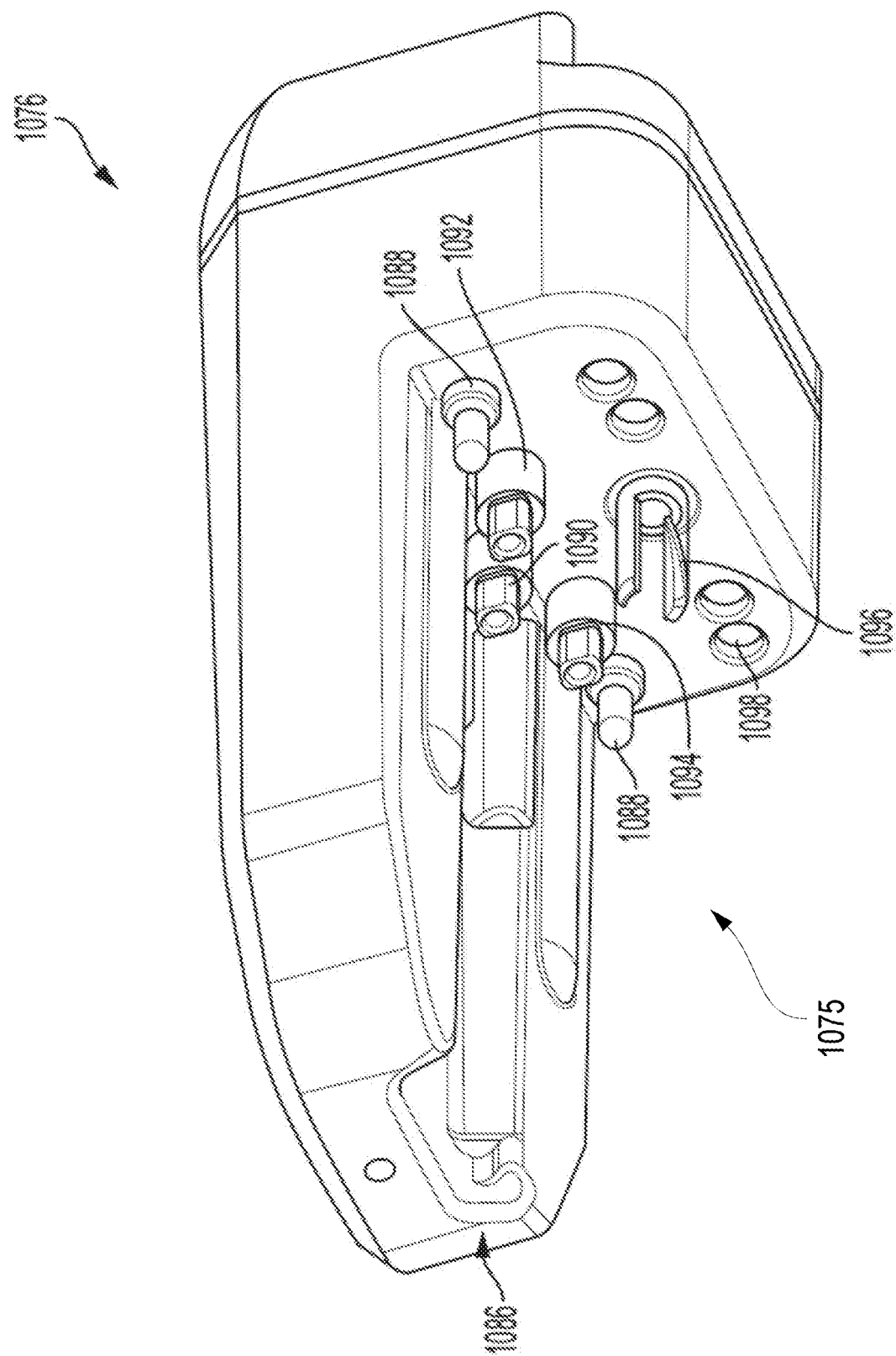
FIG. 24 is a perspective view of the detachable motor pack of FIG. 6A.

FIG. 24 shows interfacing features of the motor pack 1076. A control cable may electrically connect the motor pack 1076 to a controller. Examples of suitable controllers are described elsewhere herein. The dovetail alignment feature 1086 of the motor pack 1076 interfaces with the dovetail alignment feature 1080 of the proximal surgical tool interface 1074. Precision alignment pins 1088 are received by corresponding alignment receptacles in the proximal surgical tool interface 1074. A roll drive coupling 1090, a clamp drive coupling 1092, and a fire drive coupling 1094 together comprise an interface portion 1075 with corresponding input couplings of the proximal surgical tool interface 1074. The roll drive coupling 1090 is rotationally coupled with rotation of the instrument shaft 1072. A clamp drive coupling 1092 is used to transfer a rotary actuation motion from an electric motor in the motor pack 1076 to a clamping mechanism in the end effector. The fire drive coupling 1094 is used to transfer a rotary actuation motion from an electric motor in the motor pack 1076 to the end effector, for example, to deploy staples into clamped tissue and to articulate a knife to cut the clamped and stapled tissue. A latch shaft 1096 of the latch mechanism is configured to provide for automated latching of the motor pack 1076 to the proximal surgical tool interface 1074 in response to pushing the motor pack 1076 onto the proximal surgical tool interface 1074 along the engagement axis. Motor pack electrical contacts 1098 are positioned to interface with corresponding proximal surgical tool interface electrical contacts when the motor pack 1076 is mounted and latched to the proximal surgical tool interface 1074.

Figure 25:
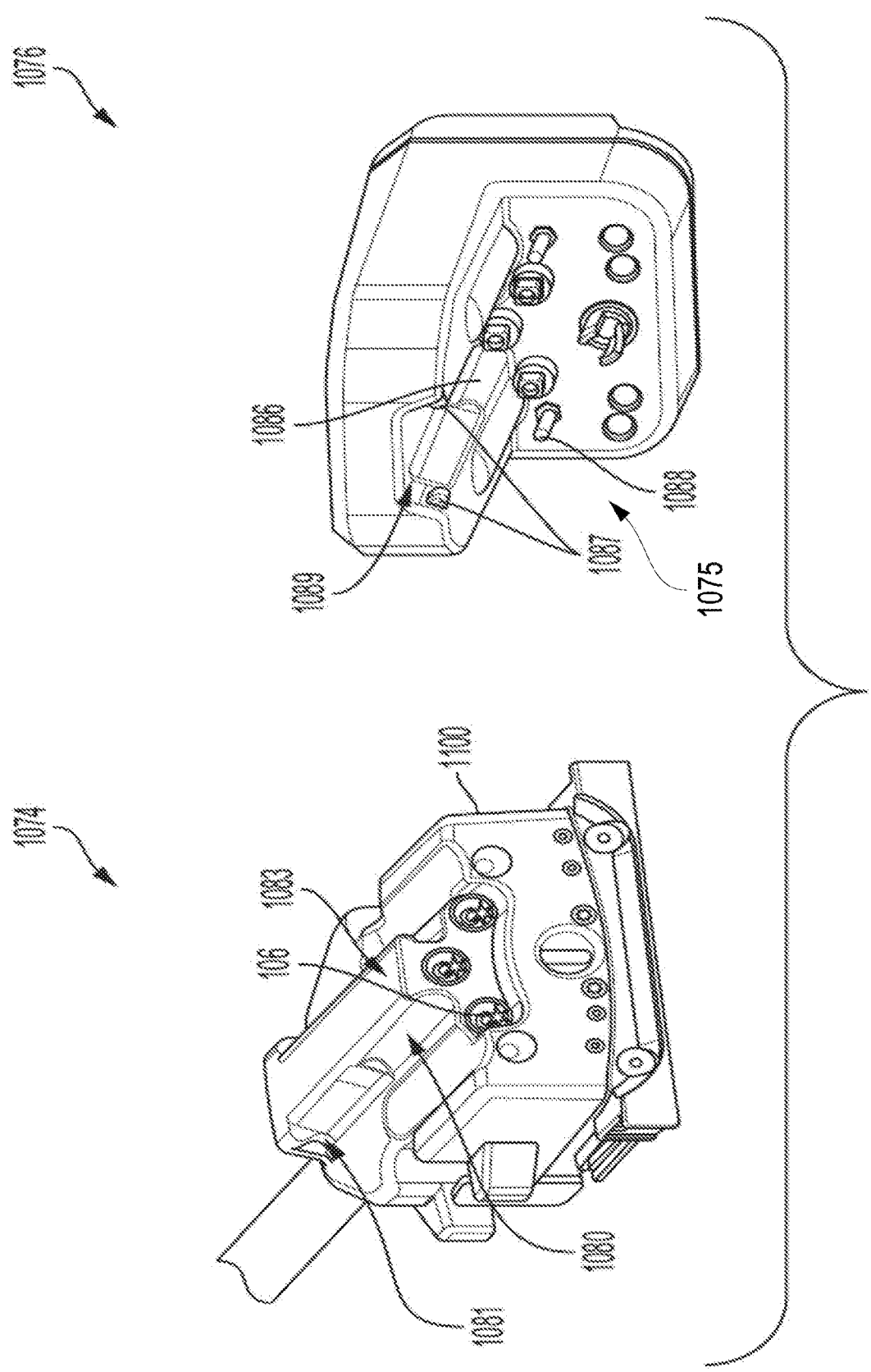
FIG. 25 is a perspective view of the robotic surgical tool of FIG. 6A depicting the proximal surgical tool interface and the second interface portion of the detachable motor pack.

FIG. 25 depicts corresponding interfacing features of the proximal surgical tool interface 1074 and the second interface portion 1075 of the motor pack 1076 that provide progressive engagement during the mounting of the motor pack 1076 on to the proximal surgical tool interface 1074 for easy, precise alignment. Easy initial engagement between the motor pack 1076 and the proximal surgical tool interface 1074 is provided by double-dove tail features of the motor pack 1076 and the proximal surgical tool interface 1074. The double-dovetail features of the proximal surgical tool interface 1074 include a pair of proximal recesses 1080, a pair of distal recesses 1081, and a flattop surface 1083 disposed over and between the proximal recesses 1080 as well as over and between the distal recesses 1081. The double-dovetail features of the motor pack 1076 include a pair of elongated proximal protrusions 1086, a pair of distal protrusions 1087, and a flat surface 1089 disposed over and between the proximal protrusions 1086 as well as over and between the distal protrusions 1087. When the motor pack 1076 is fully mounted to the proximal surgical tool interface 1074, the distal protrusions 1087 are received by the distal recesses 1081 and the proximal protrusions 1086 are received by the proximal recesses 1080, thereby securing the motor pack 1076 to the proximal surgical tool interface 1074 against all relative motion except proximal translation of the motor pack 1076 relative to the proximal surgical tool interface 1074. The gap between the proximal protrusions 1086 and the distal protrusions 1087 facilitates a coupling sequence in which the motor pack 1076 is partially overlapped with the proximal surgical tool interface 1074 so that the motor pack flat surface 1089 interfaces with the proximal surgical tool interface top surface 1083 and the proximal protrusions 1086 are disposed proximal of the proximal chassis proximal recesses 1080. The motor pack 1076 is then slid distal relative to the proximal surgical tool interface 1074, thereby causing the proximal protrusions 1086 to be slidingly received by the proximal recesses 1080. During a final portion of distal movement of the motor pack 1076 relative to the proximal surgical tool interface 1074 the distal protrusions 1087 are then received by the distal recesses 1081. The double-dovetail features accommodate a range of initial misalignment between the motor pack 1076 and the proximal surgical tool interface 1074, thereby making it easy to accomplish the initial mating between the double-dovetail features. Once initially mated, relative motion of the motor pack 1076 toward the proximal surgical tool interface 1074 results in progressively less possible misalignment between the motor pack 1076 and the proximal surgical tool interface 1074 due to the progressively longer interfacing portions of the double-dovetail features. At the end of the relative movement of the motor pack 1076 toward the proximal surgical tool interface 1074, the precision alignment pins 1088 on the motor pack 1076 engage the precision alignment receptacles 1100 in the proximal surgical tool interface 1074, thereby precisely positioning the motor pack 1076 relative to the proximal surgical tool interface 1074.

In another aspect, the detachable motor pack may include a releasably attachable power source. The controller of the detachable motor pack may be configured to detect a presence of a primary power source of the hand-held surgical instrument and to detect a presence of a primary power source of the robotic surgical instrument. In some aspects, the controller may be configured to detect the presence of a primary battery pack comprising the primary power source of the hand-held surgical instrument. In another aspect, the controller of the detachable motor pack may be configured to detect the presence of a wired power source comprising the primary power source of the robotic surgical instrument. In still another aspect, the controller may be configured to cause the releasably attached power source to source power to the hand-held surgical instrument upon a determination of a lack of presence of a primary power source of the hand-held surgical instrument. In yet another aspect, the releasably attachable power source is rechargeable.

The releasably detachable power source disclosed above may include a number of aspects. In one example, a releasably attachable power source for a detachable motor pack for use with a hand-held surgical device and a robotic surgical device, may include a housing, a plurality of batteries, and a controller, in which the controller is configured to control a voltage output and a current output of the power source. The controller may further be configured to determine if the detachable motor pack is in communication with the hand-held surgical device or in communication with the robotic surgical device. In one example, the controller of the releasably detachable power source may receive data parameters from the detachable motor pack. The data parameters may include information indicative of an attachment of the detachable motor pack to a hand-held surgical device or to a robotic surgical device. The controller of the power source may be configured to source power directly from the plurality of batteries to the detachable motor pack. The power source controller may further be configured to source power to the detachable motor pack having a voltage differing from a voltage of the plurality of batteries. In another aspect, the controller of the power source may be configured to control a voltage output and a current output of the power source based on data parameters received from the detachable motor pack.

In some instances, it may be desirable to have detachable battery packs that differ in their output characteristics. As an example, a first hand-held surgical device may require a motor pack having a first voltage output and a first output capacity, and a second hand-held surgical device may require a motor pack having a second voltage output and a second output capacity. In a second example, a first detachable surgical tool may require a power source having a first voltage output and a first output capacity, while a second detachable surgical tool may require a power source having a second voltage output and a second output capacity.

In one aspect, a single detachable battery pack may include voltage and current controls to change the output characteristics of the battery pack to meet the power requirements of either the hand-held devices or surgical tools. In another aspect, a battery pack may operate in a "native mode" to source power to the hand-held device directly from the batteries. The battery pack may also operate in a second "conditioned mode" to condition the battery power according to a variety of electronics and to source the "conditioned" power (having a voltage and/or current that differs from the native mode) to the hand-held device. Different battery packs may have different "native modes" based on the types of batteries inserted within them.

In another aspect, a detachable battery pack may be configured to accept rechargeable batteries or non-rechargeable batteries having similar form factors. In one example of the use of such a battery pack, non-rechargeable batteries may be inserted into the battery pack and the surgical instrument may be used while the rechargeable batteries are charging.

In one aspect, a detachable motor pack for use with multiple electrical surgical instruments may include a housing, a plurality of motors retained within the housing, a controller configured to control one or more operations of the plurality of motors, in which the controller includes a processor and a memory unit, a power supply interface configured to receive a releasably attachable power source, a first interface portion, in which the first interface portion is configured to releasably attach to a hand-held surgical instrument and to a robotic surgical instrument, and a second interface portion, in which the second interface portion is configured to releasably attach to a first surgical tool of the hand-held surgical instrument and to a second surgical tool of the robotic surgical instrument.

In some examples, the memory unit of the motor pack may include instructions that, when executed by the motor pack processor, cause the processor to determine one or more output parameters of a (first) power source releasably attached to the power supply interface. In some examples, the one or more output parameters may include a voltage output and a current output of the (first) power source. The memory unit of the motor pack may further include instructions that, when executed by the motor pack processor, cause the processor to store the one or more output parameters of the (first) power source in the motor pack memory unit. Additionally, the memory unit of the motor pack may include instructions that, when executed by the processor, cause the processor to determine one or more output parameters of a second power source releasably attached to the power supply interface, compare the one or more output parameters of the second power source to the one or more output parameters of the first power source, and cause the second releasably attached power source to output a voltage or a current equal to the voltage output or current output, respectively, of the first releasably attached power source. In one example, the controller of the motor pack may transmit data to a controller within the second releasably attached power source. The controller of the second power source may use those data to condition the output voltage or current of the second power source so that they are equal to those of the first power source.

Figure 26A:
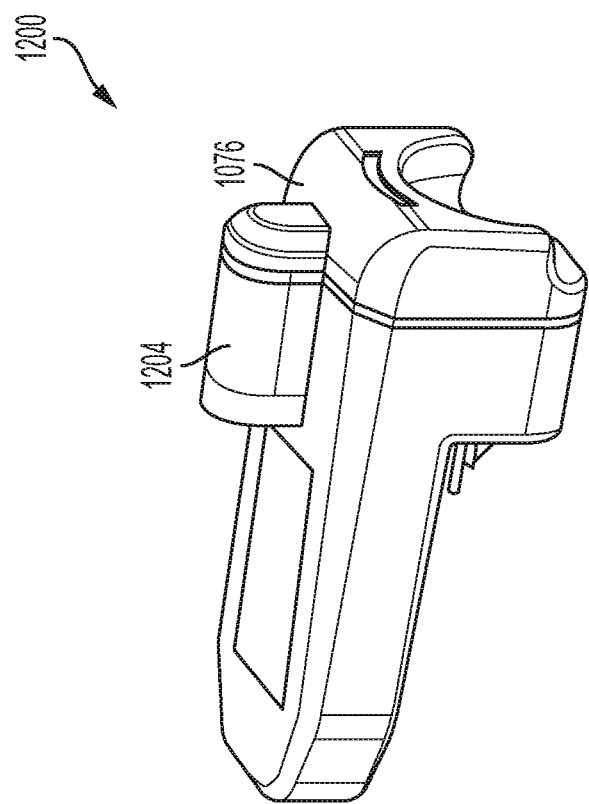
FIG. 26A is a perspective view of a detachable motor pack to which is mounted a detachable battery pack, in accordance with at least one aspect of the present disclosure.
Figure 26B:
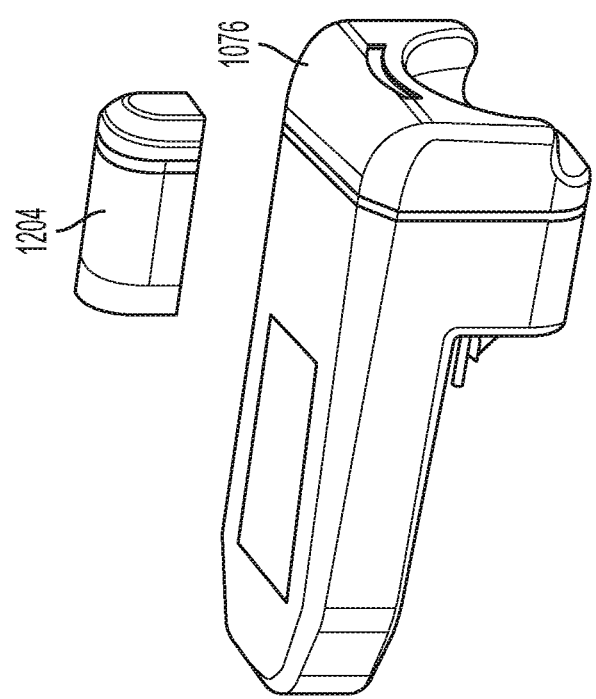
FIG. 26B is a perspective view of the detachable battery pack separated from the detachable motor pack, in accordance with at least one aspect of the present disclosure.

FIGS. 26A, 26B illustrate an example of a detachable motor pack and an associated detachable battery pack. FIG. 26A illustrates the assembled motor pack/battery pack 1200 which may include the detachable motor pack 1076 having a detachable battery pack 1204 releasably affixed to a surface of the motor pack 1076. FIG. 26B depicts the releasable motor pack 1076 separated from the detachable battery pack 1204.

In various aspects, Integrity of communications between the robotic surgical instrument and a surgical hub (e.g. surgical hub 106) such as, for example, data communications indicative of positions and/or motions of an end effector of the robotic surgical instrument are verified. In at least one aspect, accurate communications between the robotic surgical instrument and the surgical hub can be ensured using security codes such as, for example, cyclic redundancy checks (CRC) which are error-detecting codes attached to data communications to detect accidental changes in communicated data which may occur during data transmission. Blocks of data entering these systems get a short check value attached, based on the remainder of a polynomial division of their contents.

In various instances, a safety processor is configured to stop the motor pack from running if a computed CRC, which is computed from the received data, does not match the received CRC. A CRC verification module can be employed by the safety processor to compute a CRC from the received data and compare the computed CRC with the received CRC. In various instances, processors of the robotic surgical instrument and/or the surgical hub may comprise security code generator modules and/or security code verification modules. Security codes can be generated by CHECK-SUM, HASH, or other suitable protocols. The security code generation module and/or the security code verification module may be implemented in hardware, firmware, software or any combination thereof.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A detachable motor pack for use with multiple electrical surgical instruments, the detachable motor pack comprising:
a housing;
a plurality of motors retained within the housing;
a controller configured to control one or more operations of the plurality of motors;
a first interface portion, wherein the first interface portion is configured to releasably attach to a hand-held surgical instrument and to a robotic surgical instrument; and
a second interface portion, wherein the second interface portion is configured to releasably attach to a first surgical tool of the hand-held surgical instrument and to a second surgical tool of the robotic surgical instrument,
wherein the controller is configured to control a first set of operations of the plurality of motors when the detachable motor pack is releasably attached to the hand-held surgical instrument, and to control a second set of operations of the plurality of motors when the detachable motor pack is releasably attached to the robotic surgical instrument.

2. The detachable motor pack of claim 1, further comprising a user display unit, wherein the controller is configured to control the user display unit.

3. The detachable motor pack of claim 1, further comprising one or more electrical contacts configured to source electrical signals to one or more mating electrical contacts of the hand-held surgical instrument thereby providing data to a user display unit of the hand-held surgical instrument.

4. The detachable motor pack of claim 1, wherein the controller is configured to receive one or more operating parameters from the first surgical tool and the second surgical tool.

5. The detachable motor pack of claim 4, wherein the controller is configured to control the first set of operations based on the one or more operating parameters received from the first surgical tool, and wherein the controller is configured to control the second set of operations based on the one or more operating parameters received from the second surgical tool.

6. A detachable motor pack for use with multiple electrical surgical instruments, the detachable motor pack comprising:
a housing configured to receive a releasably attachable power source;
a plurality of motors retained within the housing;
a controller configured to control one or more operations of the plurality of motors;
a first interface portion, wherein the first interface portion is configured to releasably attach to a hand-held surgical instrument and to a robotic surgical instrument; and
a second interface portion, wherein the second interface portion is configured to releasably attach to a first surgical tool of the hand-held surgical instrument and to a second surgical tool of the robotic surgical instrument,
wherein the controller is configured to detect a presence of a primary power source of the hand-held surgical instrument or to detect a presence of a primary power source of the robotic surgical instrument.

7. The detachable motor pack of claim 6, wherein the controller is configured to detect the presence of a primary battery pack comprising the primary power source of the hand-held surgical instrument.

8. The detachable motor pack of claim 6, wherein the controller is configured to detect the presence of a wired power source comprising the primary power source of the robotic surgical instrument.

9. The detachable motor pack of claim 6, wherein the controller is configured to cause the releasably attached power source to source power to the hand-held surgical instrument upon a determination of a lack of presence of the primary power source of the hand-held surgical instrument.

10. The detachable motor pack of claim 6, wherein the releasably attachable power source is rechargeable.

11. A releasably attachable power source for a detachable motor pack for use with multiple electrical surgical instruments, the releasably attachable power source comprising:
a housing;
a plurality of batteries; and
a controller, wherein the controller is configured to control a voltage output and a current output of the releasably attachable power source, and wherein the controller is configured to determine when the detachable motor pack is in communication with a hand-held surgical device or in communication with a robotic surgical device,
wherein the controller is configured to control the voltage output and the current output of the releasably attachable power source based on data parameters received from the detachable motor pack.

12. The releasably attachable power source of claim 11, wherein the controller is configured to source power directly from the plurality of batteries to the detachable motor pack.

13. The releasably attachable power source of claim 11, wherein the controller is configured to source power to the detachable motor pack having a voltage differing from a voltage of the plurality of batteries.

14. The releasably attachable power source of claim 11, wherein the data parameters comprise information indicative of an attachment of the detachable motor pack to the hand-held surgical device or to the robotic surgical device.

15. A detachable motor pack for use with multiple electrical surgical instruments, the detachable motor pack comprising:
a housing;
a plurality of motors retained by the housing;
a controller configured to control one or more operations of the plurality of motors, wherein the controller comprises a processor and a memory unit;
a power supply interface configured to receive a releasably attachable power source;
a first interface portion, wherein the first interface portion is configured to releasably attach to a hand-held surgical instrument and to a robotic surgical instrument; and
a second interface portion, wherein the second interface portion is configured to releasably attach to a first surgical tool of the hand-held surgical instrument and to a second surgical tool of the robotic surgical instrument, wherein the memory unit comprises instructions that, when executed by the processor, cause the processor to determine one or more output parameters of the releaseably attachable power source releasably attached to the power supply interface.

16. The detachable motor pack of claim 15, wherein the one or more output parameters comprise a voltage output and a current output of the releasably attachable power source.

17. The detachable motor pack of claim 15, wherein the memory unit comprises instructions that, when executed by the processor, cause the processor to store the one or more output parameters of the releasably attachable power source in the memory unit.

18. The detachable motor pack of claim 16, wherein the memory unit comprises instructions that, when executed by the processor, cause the processor to:
- determine one or more output parameters of a second releasably attachable power source releasably attachable to the power supply interface;
- compare the one or more output parameters of the second releasably attachable power source to the one or more output parameters of the releasably attachable power source; and
- cause the second releasably attachable power source to output a voltage or a current equal to the voltage output or current output, respectively, of the releasably attachable power source.

* * * * *